United States Patent [19]

Caruthers et al.

[11] Patent Number: 5,218,103

[45] Date of Patent: Jun. 8, 1993

[54] NUCLEOSIDE THIOPHOSPHORAMIDITES

[75] Inventors: Marvin H. Caruthers, Boulder, Colo.; Yun-Xi Ma, Mississauga, Canada; Eric K. Yau, Kirkland, Wash.; John Nielsen, Horsholm, Denmark; Wolfgang Brill, Freiburg, Fed. Rep. of Germany

[73] Assignee: University Patents, Inc., Westport, Conn.

[21] Appl. No.: 643,381

[22] Filed: Jan. 22, 1991

Related U.S. Application Data

[63] Continuation-in-part of Ser. No. 417,387, Oct. 5, 1989, abandoned, which is a continuation-in-part of Ser. No. 314,011, Feb. 22, 1989, abandoned, which is a continuation-in-part of Ser. No. 198,886, May 26, 1988, abandoned.

[51] Int. Cl.$^5$ .............. C07H 19/10; C07H 19/20; C07H 21/00
[52] U.S. Cl. .............. 536/25.33; 536/26.72; 536/26.5; 536/26.8; 536/26.71; 568/18
[58] Field of Search .............. 536/27, 28, 29; 568/18

[56] References Cited

U.S. PATENT DOCUMENTS

| | | | |
|---|---|---|---|
| 3,451,997 | 6/1969 | Fujimoto et al. | 536/29 |
| 3,687,808 | 8/1972 | Merigan, Jr. et al. | 536/28 |
| 3,846,402 | 11/1974 | Erkstein et al. | 536/29 |
| 3,853,844 | 12/1974 | Shuman et al. | 536/29 |
| 4,373,071 | 2/1983 | Itakura | 525/375 |
| 4,415,732 | 11/1983 | Caruthers et al. | 536/29 |
| 4,458,066 | 7/1984 | Caruthers et al. | 536/27 |
| 4,500,707 | 2/1985 | Caruthers et al. | 536/27 |
| 4,668,777 | 5/1987 | Caruthers et al. | 536/27 |
| 4,728,730 | 3/1988 | Frey et al. | 536/28 |
| 4,808,708 | 2/1989 | Yoshida et al. | 536/27 |

OTHER PUBLICATIONS

Matsukura et al. 1987, Proc. Natl. Acad. Sci. vol. 84, pp. 7706–7710.
Stec et al. 1984, J. Am. Chem. Soc. vol. 106, pp. 6077–6079.
Eckstein, F. 1970, J. Am. Chem. Soc. vol. 92, No. 15, pp. 4718–4723.
Froehler, B. C. 1986, Tetrahedron Letters, vol. 27, No. 46, pp. 5575–5578.
Stein et al. 1988, Nucleic Acids Res. vol. 16, No. 8, pp. 3208–3221.
Sekine et al. 1979, J. Organic Chem. vol. 44, No. 13, pp. 2325–2326.

*Primary Examiner*—Johnnie R. Brown
*Assistant Examiner*—Gary L. Kunz
*Attorney, Agent, or Firm*—Yahwak & Associates

[57] ABSTRACT

The present invention relates to new and useful nucleoside thiophosphoramidite, polynucleotide dithioate phosphoramidite and polynucleotide phosphorothioamidate phosphoramidite compounds as well as the process whereby these compounds can be used for synthesizing new mononucleotides and polynucleotides having phosphorodithioate, phosphorothioamidate, phosphorothiotriesters and phosphorothioate internucleotide linkages.

26 Claims, No Drawings

NUCLEOSIDE THIOPHOSPHORAMIDITES

The inventions described herein were supported, in part, with federal funds under a grant or award from the Department of Health, Education, and Welfare. Accordingly, the United States Government has certain statutory rights to the invention described herein under 35 U.S.C. 200 et seq.

This is a continuation-in-part application of earlier filed U.S. patent application No. 07/417,387, filed on Oct. 5, 1989, now abandoned, which in turn is a continuation in part of earlier filed U.S. patent application Ser. No. 07/314,011, filed on Feb. 22, 1989, now abandoned, which in turn is a continuation in part of U.S. patent application Ser. No. 07/198,886, filed on May 26, 1988, now abandoned.

This invention described and claimed herein relates to novel and useful phosphorous compounds which are particularly useful in the production of polynucleotides having analogs attached to phosphorous.

The present invention relates to novel and useful nucleoside thiophosphoramidite, polynucleotide dithioate phosphoramidite, polynucleotide phosphoramidite, nucleoside 3'-hydrogenphosphonodithioates, nucleosid-3'-yl-S-aralkylphosphorodithioate, nucleoside 3'-hydrogenphosphonothioate, nucleoside 3'-methylphosphonothioate, dinucleoside H-phosphonothioate, dinucleoside phosphorodithioate and nucleoside 3'-amidophosphorodithioate compounds as well as the processes whereby these compounds can be used for synthesizing novel mononucleotides and polynucleotides having phosphorodithioate, methylphosphonothioate and H-phosphonothioate internucleotide linkages, and phosphorothioamidate, phosphorothiotriester, and phosphorothioate substituents. These novel mononucleotides and polynucleotides can be used for many biological, therapeutic and diagnostic applications. Potential therapeutic applications include treating tumors, viral infections and bacterial infections. Additionally, these compounds can be used to deliver to specific sites in cells and tissues such reagents as metal ions, toxins, intercalating agents and other reagents that alter the biochemical reactivity of polynucleotides and proteins. These compounds can also be joined to sugars, steroids, proteins, peptides and lipids so as to deliver these oligonucleotides to specific cells and thus to target certain cells for various biological and therapeutic applications with these oligonucleotide analogs. These compounds can also be used for various diagnostic purposes. By attaching fluorescent or other chemically reactive reagents, antigens, antibodies, proteins, and metal ions to these compounds, they can be used for diagnosing diseases and the normal and abnormal biochemistry of cells, tissues and body fluids such as blood and urine. There are also many uses in modern biology and chemistry as well. For example, these compounds can be used to develop improved methods for sequencing and cutting DNA, for imaging in X-ray crystallography, NMR, and electron microscopy, and for studying enzyme reactions.

High yielding methodologies are currently available for the rapid synthesis of sequence defined polynucleotides having the natural internucleotide linkage (Caruthers, M. H., Science 230, 281-285, 1985; Caruthers, M.H. and Beaucage, S. L., U.S. Pat. No. 4,425,732; Caruthers, M.H. and Matteucci. U.S. Pat. No. 4,458,066). An important step in this process is oxidation of the intermediate phosphite triester to the naturally occurring phosphate triester with aqueous iodine. These phosphite triesters can also be oxidized under anhydrous conditions with amines or ammonia and iodine to yield variable reported amounts of oligonucleotide phosphoramidates or with sulfur to yield oligonucleotide phosphorothioates (Uznanski, B. Koziolkiewicsz, M., Stec. W. J., Zon, G., Shinozuka, K. and Marzili, L., Chemica Scripta 26, 221-224, 1986; Nemer, M.H. and Ogilvie, K.K., Tetrahedron Letter 2 21, 4149-4152, 1980). Other methods employing H-phosphonate internucleotide linkages can also be used to synthesize oligonucleotide phosphoramidates and oligonucleotide phosphorothioates (Froehler, B.C., Tetrahedron Letters 27, 5575-5578, 1986). A process has also been developed for synthesizing methylphosphonothioate internucleotide linkages (Brill, W.K.-D. and Caruthers, M. H., Tetrahedron Letters 28, 3205-3208, 1987). Unfortunately, none of these procedures can be used to synthesize polynucleotides containing the phosphorodithioate or the phosphorothioamidate internucleotide linkages.

The production of uridine 2',3'- cyclic phosphorodithioate is described in the literature (F. Eckstein, J. Am. Chem. Soc. 92, 4718-4732, 1970. Unfortunately, the process cannot be used to synthesize deoxynucleoside phosphorodithioates or nucleoside phosphorodithioates useful for synthesizing polynucleotides containing the dithioate linkage. The procedure also yields a mixture of mononucleotides having phosphorodithioate and phosphorothioate moieties. Additionally the yield or uridine 2',3'-cyclic phosphorodithioate is only 28% and the acidity of $P_2S_5$ and the high temperatures used in the synthesis of the cyclic phosphorodithioate would preclude the use of this procedure with protected deoxyadenosine which would undergo depurination.

Similarly, adenosine cyclic 3',5'-phosphorodithioate can be synthesized by treating suitably protected adenosine with 4-nitrophenylphosphoranilidochloridothioate followed by cyclization with potassium t-butoxide and conversion to the dithioate in a reaction with sodium hydride/carbon disulfide (J. Boraniak and W. Stec, J. Chem. Soc, Trans. I, 1645, 1987). Unfortunately these reaction conditions and the low synthesis yields preclude the use of this chemistry for synthesizing oligonucleotides having the phosphorodithioate linkages.

In general, the compounds, according to the present invention, can be represented by general formulae Ia, Ib, and IIa-f.

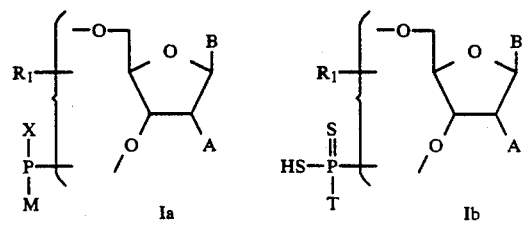

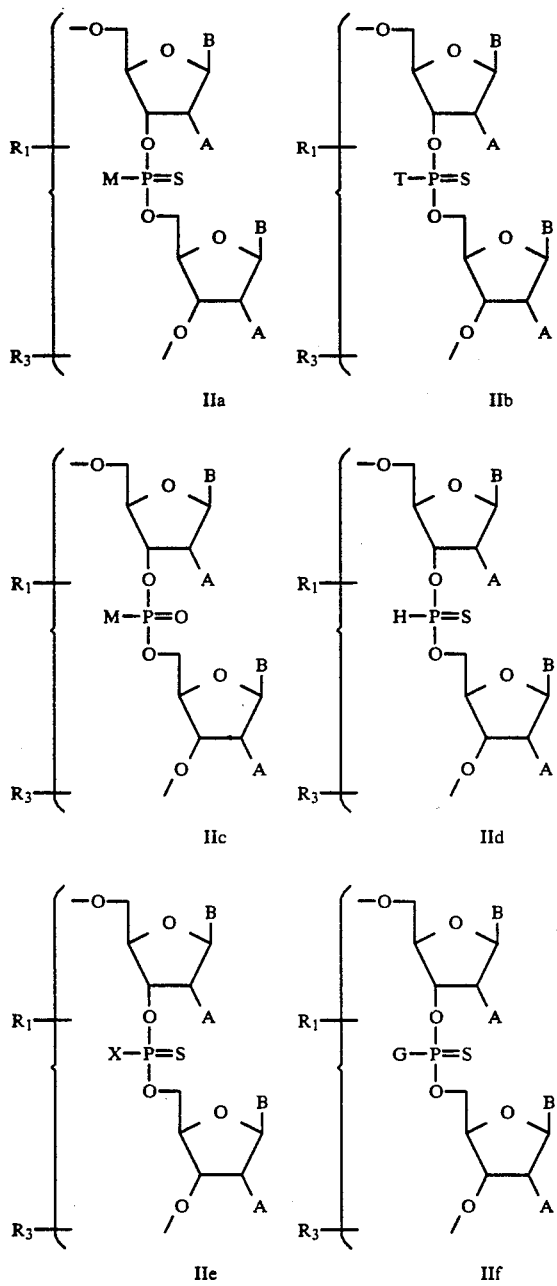

Where, throughout the following description, $R_1$ is H or a blocking group; A is D or $DR_2$ where D is OH, H, halogen, SH, $NH_2$ or azide and $DR_2$ is oxygen, sulfur or nitrogen as D and $R_2$ is a heteroatom substituted or unsubstituted blocking group; B is a nucleoside or deoxynucleoside base; $R_3$ is H or a blocking group, and T, G, X and M are substituents where heteroatoms are linked covalently to phosphorous. Substituents T, G, X and M may also be covalently linked to heteroatom substituted or unsubstituted alkyl, aryl, aralkyl, cycloalkyl, cycloalkylakyl, alkenyl, cycloalkenyl, alkynyl, aralkynyl or cycloalkynyl groups. The compounds of general formulae I and II wherein T, G, X and M are substituents where heteroatoms are linked to phosphorus include those in which the heteroatoms are sulfur, nitrogen and oxygen.

The novel compounds of general formula I are of two classes, Ia and Ib; class Ia consists of those in which phosphorus is single bonded to each of two substituents, X and M, through the heteroatoms; and class Ib are those in which phosphorous is single and double bonded to sulfur and also to one other substituent through the group T. These compounds are useful for synthesizing polynucleotides containing phosphorodithioate, phosphorothioamidate, phosphorothioate triesters and phosphorothioate internucleotide linkages and for various biological uses.

Compounds of general formula II are those in which phosphorus bonded to sulfur or oxygen and single bonded to hydrogen or the substituents T, G, X or M. The preferred compounds are those with phosphorous and to either H or $R_4$ where $R_4$ is a heteroatom substituted or unsubstituted alkyl, aryl, aralkyl, cycloalkyl, cycloalkylalkyl, alkenyl, cycloalkenyl, aralkenyl, alkynyl, aralkynyl or cycloalkynyl group. The substituent M is sulfur single bonded to phosphorous and to $R_5$ where $R_5$ is a heteroatom substituted or unsubstituted alkyl, aryl, aralkyl, cycloalkyl, cycloalkylalkyl, alkenyl, cycloalkenyl, aralkenyl, alkynyl, aralkynyl or cycloalkynyl. The substituents G and X are nitrogen single bonded to phosphorous where G is amino or primary amino, $NHR_6$, and X is secondary amino $NR_6R_7$. $R_6$ and $R_7$ when taken together form an alkylene chain containing up to 5 carbon atoms in the principal chain and a total of up to 10 carbon atoms with both terminal valence bonds of said chain being attached to the nitrogen atom to which $R_6$ and $R_7$ are attached; and where $R_6$ and $R_7$ taken separately each represent hetroatom substituted or unsubstituted alkyl, aryl, aralkyl, cycloalkyl, cycloalkylalkyl, alkenyl, cycloalkenyl, aralkenyl, alkynyl, aralkynyl, or cycloalkynyl groups; and $R_6$ and $R_7$ when taken together with the nitrogen atom to which they are attached may also form a nitrogen heterocycle including at least one additional heteroatom from the group consisting of nitrogen, oxygen or sulfur; and $R_6$ and $R_7$ when taken together with the nitrogen atom to which they are attached may also form a ring nitrogen heterocycle compound which contains unsaturated bonds in the ring structure and may also contain at least one additional heteroatom from the group consisting of nitrogen, oxygen or sulfur. Compounds of general formula II may also be those in which oxygen is double bonded to phosphorous plus M which is single bonded to phosphorous. Compounds II are useful for various biological uses and for synthesizing polynucleotides containing phosphorodithioate, phophorothioamidate, phosphorothioate triester and phosphorothioate internucleotide linkages which are also useful for biological studies.

Amines from which the substituent group G can be derived include a wide variety of primary amines such as methylamine, ethylamine, propylamine, isopropylamine, aniline, cyclohexylamine, benzylamine, polycyclic amines, heteroatom substituted aryl or alkylamines, and similar primary amines. Amines from which the substituent group X can be derived include a wide variety of secondary amines such as dimethylamine, diethylamine, diisopropylamine, dibutylamine, methylpropylamine, methylhexylamine, methylcyclopropylamine, ethylclohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

The nucleoside and deoxynucleoside bases represented by B in the above formulae are well known and include purines, e.g. adenine, hypoxanthine, quanine, and their derivatives, and pyrimidines, e.g. cytosine, uracil, thymine, and their derivatives.

The blocking groups represented by $R_1$, $R_2$ and $R_3$ in the above formulae include trityl, methoxytrityl, dimethoxytrityl, pivalyl, acetyl, tetrahydropyranyl, methoxytetrehydropyranyl, phenoxyacetyl, isobutyloxycarbonyl, t-butyldimethylsilyl, triisopropylsilyl, alkyl or aryl carbonoyl, and similar blocking groups well known in the art. Common blocking groups represented by $R_4$ and $R_5$ include 4-chlorobenzyl, 2,4-dichlorobenzyl, and β-cyanoethyl. Although $R_{1-9}$ can represent blocking groups and in many cases these blocking groups are removed at some point during synthesis, these radicals may also remain covalently attached to nucleosides, nucleotides, and polynucleotides following synthesis and correspond to fluorescent probes, antigens, steriods, sugars, peptides, proteins, lipids or other groups that are useful for a large number of therapeutic, diagnostic, biological or biochemical applications.

As used herein the symbols for nucleotides and polynucleotides are according to the IUPAC-IUB Commission of Biochemical Nomenclature recommendations (Biochemistry 9, 4022, 1970). Several chemical terms as used in this invention are further defined as follows: These definitions apply unless, in special cases, these terms are defined differently:

alkyl— a non-cyclic branched or unbranched hydrocarbon radical having from 1 to 20 (preferably 1 to 12) carbon atoms. Heteroatoms, preferably oxygen, sulfur, or nitrogen can replace or be bonded to the carbon atoms, preferably 1 to 4 carbon atoms in this non-cyclic branched or unbranched radical. Certain heteroatoms such as halogens can be bonded to the carbon atoms in this radical.

aryl—an organic radical derived from an aromatic hydrocarbon by the removal of one hydrogen atom. This radical can contain one or more heteroatoms, preferably sulfur, nitrogen, or oxygen, as part of the aromatic ring system. Heteroatoms, preferably halogen, sulfur, oxygen, or nitrogen, can also replace hydrogen attached to carbon that is part of the ring system.

aralkyl—an organic radical in which one or more aryl radicals, preferably 1 to 3, are substituted for hydrogen atoms of an alkyl radical.

cycloalkyl—a cyclic hydrocarbon radical containing from 3 to 20 (preferably 4 to 12) carbons with 4 to 10 carbons being in the cycle ad the remainder attached to the cycle. Heteroatoms, preferably oxygen, sulfur, and nitrogen, can replace or be bonded to the carbon atoms in this cyclic hydrocarbon radical. Certain heteroatoms such as halogens can be bonded to the carbon atoms in this cyclic radical.

cycloalkylalkyl—an organic radical in which one or more cycloalkyl radicals, preferably 1 to 3, are substituted for hydrogen atoms of an alkyl radical containing from 1 to 20 atoms, preferably 1 to 12 carbon atoms.

alkenyl—an aliphatic, unsaturated, branched or unbranched hydrocarbon having at least one double bond and 2 to 20 (preferably 3 to 10) carbons. Heteroatoms, preferably sulfur, oxygen, and nitrogen, can replace saturated carbon atoms in this radical or be bonded to the saturated carbon atoms. Heteroatoms such as halogens can be bonded to the saturated carbon atoms. Heteroatoms such as oxygen, sulfur, and nitrogen can also replace carbon at an unsaturated position to generate ketone, thioketone, or imine, respectively. carbon at an unsaturated position to generate ketone, thioketone, or imine, respectively.

aralkenyl—an organic radical with one or more aryl radicals, preferably 1 to 3, are substituted for hydrogen atoms of an alkenyl radical.

cycloalkenyl—a cyclic hydrocarbon radical having from 3 to 20 (preferably 4 to 12) carbons, and at least one double bond. The cyclic part of this radical would be preferable 50 to 10 carbon atoms with the remainder attached to the cycle. The cyclic part of this radical would be preferably 5 to 10 carbon atoms with the remainder attached to the cycle. Heteroatoms, preferably oxygen, sulfur and nitrogen, can replace saturated carbons in this radical or be bonded to the saturated carbons. Heteroatoms such as halogens can be bonded to the carbon atoms in this radical.

alkynyl—an aliphatic, unsaturated branched or unbranched hydrocarbon radical containing at least one triple bond and 2 to 20 (preferably 3 to 10) carbons. Heteroatoms, preferably oxygen, sulfur, and nitrogen, can replace or be bonded to saturated carbons in this radical. Heteroatoms such as nitrogen can be replaced carbon at an unsaturated position to generate a nitrile.

aralkynyl—an organic radical in which one or more aryl groups, preferably 1 to 3, are substituted for the hydrogen atoms of an alkynyl radical.

cycloalkynyl—a cyclic hydrocarbon radical containing from 6 to 20 carbon atoms, preferably 7 or 12 carbon atoms, and at least one triple bond in the cycle with the remaining carbon atoms attached to the cycle, Heteroatoms, preferably oxygen, sulfur, and nitrogen, can replace saturated carbon atoms in this radical. Heteroatoms such as halogens can be bonded to the saturated carbon atoms.

Heteroatom substituted radicals—In all these radicals, including alkyl, aryl, aralkyl, cycloalkyl, cycloalkylalkyl, alkenyl, aralkenyl, cycloalkenyl, alkynyl, aralkynyl, and cycloalkynyl, heteroatoms, preferably sulfur, oxygen, nitrogen, and halogens, can replace hydrogen atoms attached to carbons. As described in the definition for each radical, heteroatoms, preferably oxygen, sulfur and nitrogen, can replace carbon atoms at saturated positions in alkyl, aralkyl, cycloalkyl, cycloalkylalkyl, alkenyl, arakenyl, cycloalkenyl, alkynyl, aralkynyl, and cycloalkynyl radicals. Heteroatoms, preferably sulfur, oxygen and nitrogen can also replace carbon as part of the aromatic ring system in aryl radicals. Heteroatoms can also replace carbon atoms as part of unsaturated systems such as where oxygen replaces carbon in an alkene to generate a ketone or aldehyde and nitrogen replaces carbon in an alkyne to generate a nitrile. Examples of common heteroatoms substituted radicals used in nucleotide chemistry are β-cyanoethyl, 4-chlorobenzyl, 2,4-dichlorobenzyl, 4-chlorophenyl, 2,4-dichlorophenyl, acetyl, tetrahydropyranyl, di-p-methoxytrityl, and benzoyl radicals.

phosphorodithioate internucleotide linkage—an internucleotide linkage having the general formula 5'-nucleoside-O-PS2-O-nucleoside-3' which can be illustrated with the following structure where B and A are as defined previously:

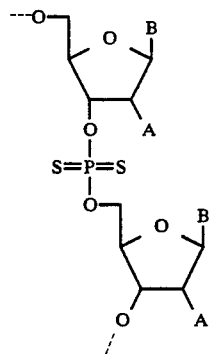

phosphorothioate internucleotide linkage—an internuleotide linkage having the general formula 5'-nuleoside-OPOS-O-nucleoside 3' which can be illustrated with the following structure where B and A are as defined previously:

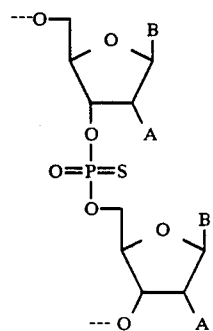

phosphorothioamidate internucleotide linkage—an internucleotide linkage having the general formula 5'-nucleoside-O-PSNHR6-O-nucleoside-3' and 5'-nucleoside-O-PSNR6R7-O-nucleoside-3' which can be illustrated with the following structures where B and A are as previously defined:

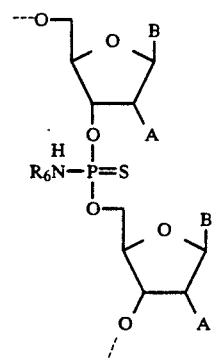

S-alkyl or S-arylphosphorothiotriester internucleotide linkage—an internucleotide linkage having the general formula 5'-nucleoside-O-POSR5-O-nucleoside-3' which can be illustrated with the following structure where B, A, and R5 are as previously defined:

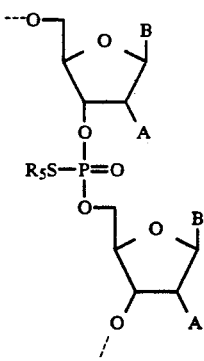

O-alkyl or arylphosphorothiotriester internucleotide linkage—an internucleotide linkage having the general formula 5'-nucleoside-O-PSOR4-O-nucleoside-3'' which can be illustrated with the following structure where B, A and R4 are previously defined:

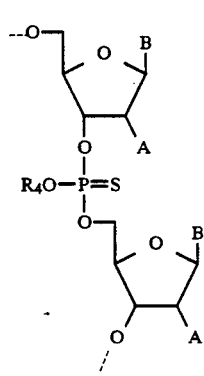

H-phosphonothioate internucleotide linkage—an internucleotide linkage having the general formula 5'-nucleoside-O-PSH-O-nucleoside-3' which can be illustrated with the following structure where B and A are as previously defined:

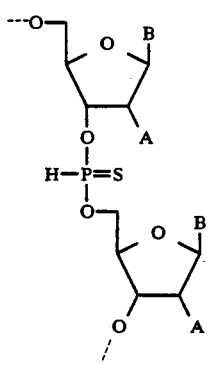

The general reaction scheme A for synthesizing compounds Ia, VIIa, and VIIb from which the preferred compounds Ia, IIa and IIc are a subset is shown in the following overview:

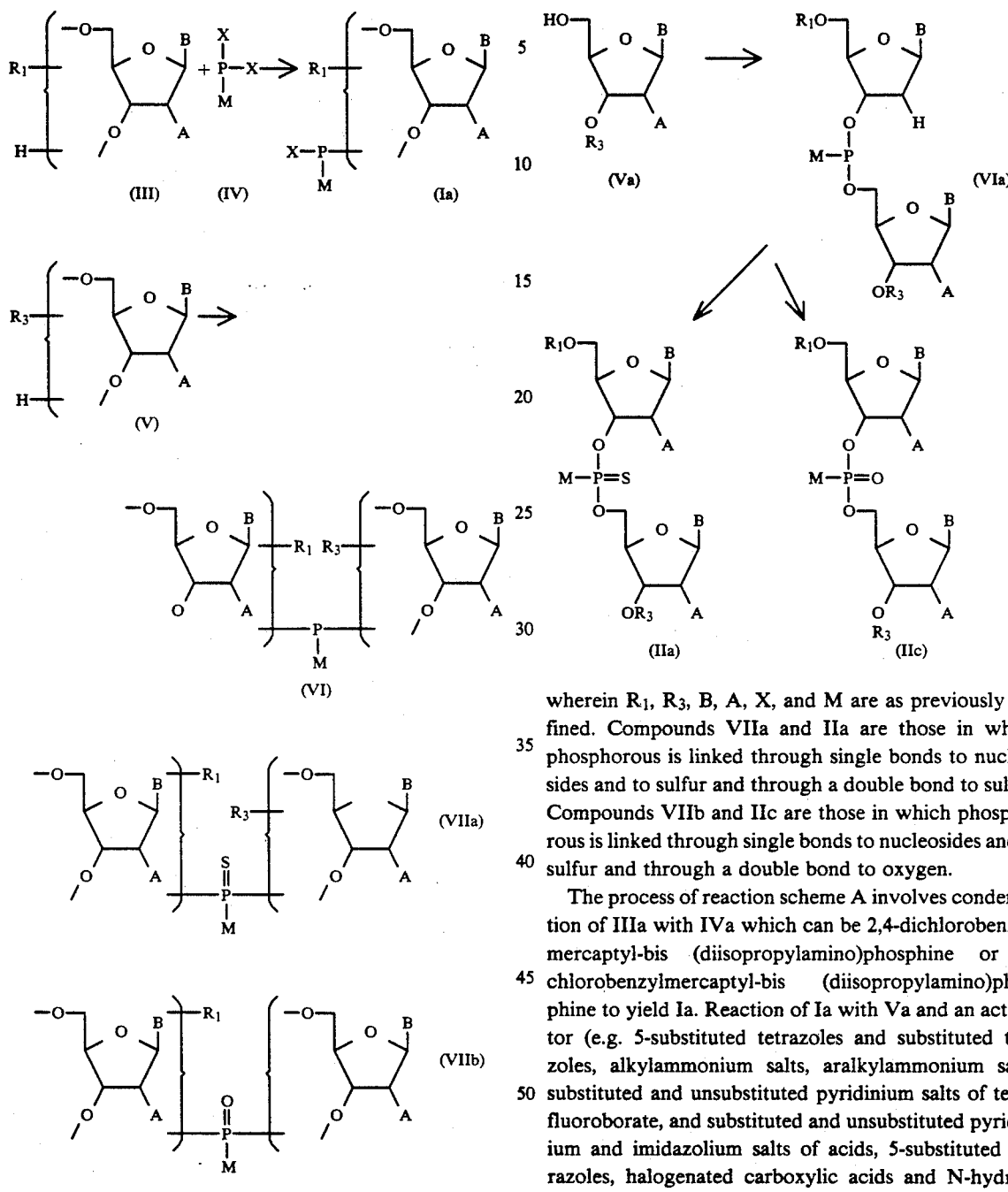

wherein $R_1$, $R_3$, B, A, X, and M are as previously defined. Compounds VIIa and IIa are those in which phosphorous is linked through single bonds to nucleosides and to sulfur and through a double bond to sulfur. Compounds VIIb and IIc are those in which phosphorous is linked through single bonds to nucleosides and to sulfur and through a double bond to oxygen.

The process of reaction scheme A involves condensation of IIIa with IVa which can be 2,4-dichlorobenzylmercaptyl-bis (diisopropylamino)phosphine or 4-chlorobenzylmercaptyl-bis (diisopropylamino)phosphine to yield Ia. Reaction of Ia with Va and an activator (e.g. 5-substituted tetrazoles and substituted triazoles, alkylammonium salts, aralkylammonium salts, substituted and unsubstituted pyridinium salts of tetrafluoroborate, and substituted and unsubstituted pyridinium and imidazolium salts of acids, 5-substituted tetrazoles, halogenated carboxylic acids and N-hydroxybenzotriazole) yields VIa, the dinucleoside 2,4-dichlorobenzylthiophosphite or dinucleoside 4-chlorobenzylthiophosphite, which can be preferably oxidized with sulfur to yield IIa, the dinucleoside phosphorodithioate triester. Of course oxidation with t-butylperoxide yields IIc, the corresponding dinucleoside phosphorothioate triester.

A second reaction scheme B was also discovered for the purpose of synthesizing compounds IIa and additionally IIb, IId, IIe, and IIf. The general reaction scheme B for synthesizing compounds IIa, IIb, IId, IIe and IIf is as follows:

The preferred reaction scheme A for synthesizing compounds Ia, IIa, and IIc is represented as follows:

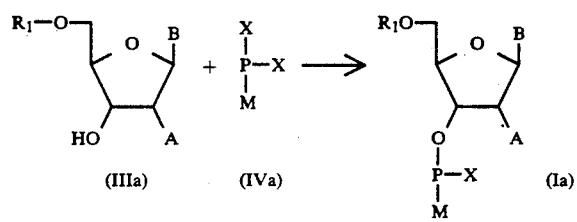

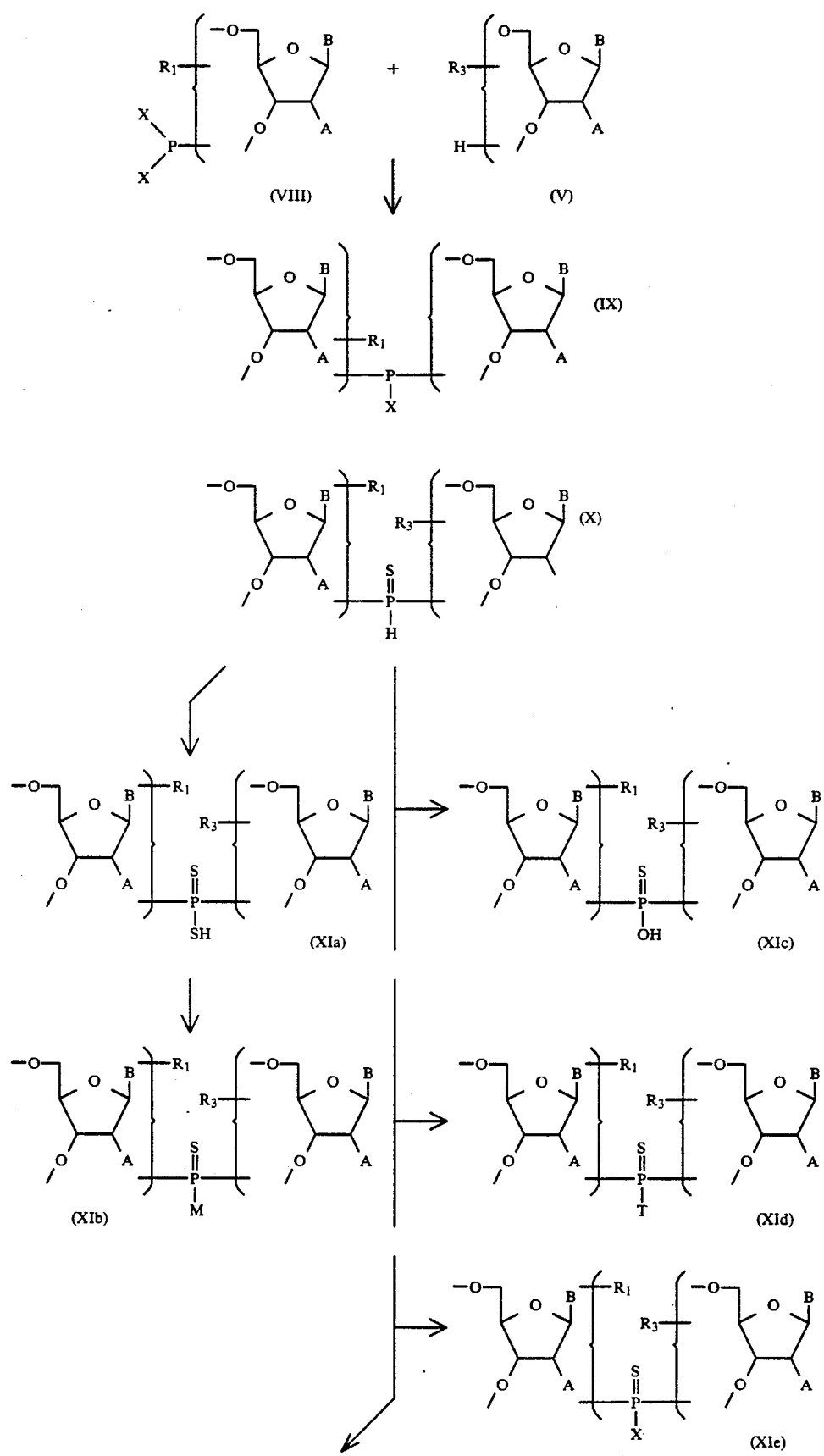

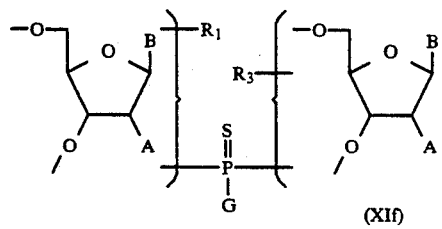
(XIf)

The preferred reaction scheme B is represented as follows:

tion of IXa with H$_2$S and an activator such as tetrazole yields the dinucleoside H-phosphonothioate, IId, which

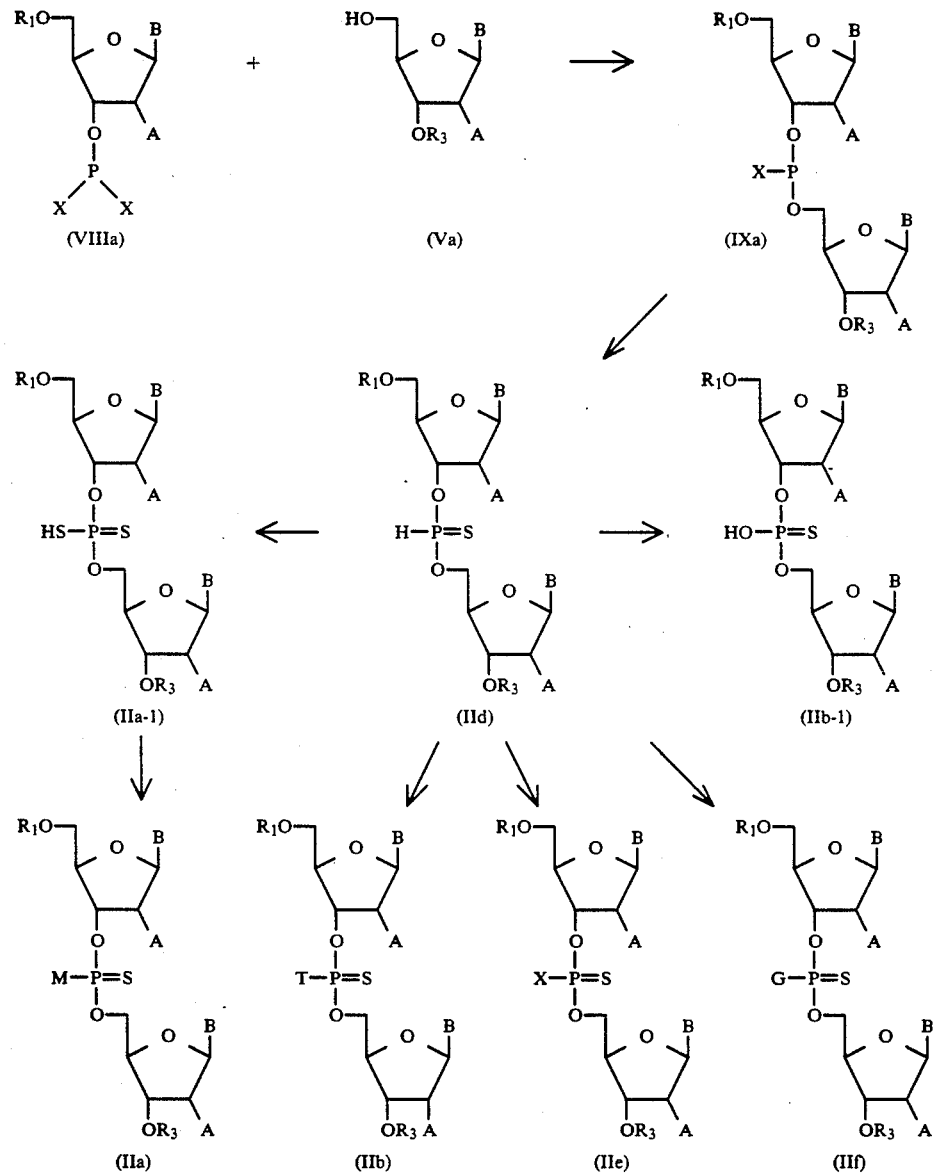

wherein R$_1$, R$_3$, B, A, X, M, G and T are as previously defined. Compounds IIa, IIa-1, IIb, IIb-1, IId, IIe, and IIf are those in which phosphorous is double bonded to sulfur and single bonded to nucleosides and one other substituent from the group of substituents including hydrogen, X, M, T and G.

The process of reaction scheme B involves synthesis of VIIIa and condensation with Va to yield IXa. Reaccan be chemically converted by oxidation with sulfur to IIa-1, the dinucleoside phosphorodithioates; by oxidation with iodine in the presence of amines to IIe or IIf, the phosphorothioamidates; by alkylation of the dinucleoside phosphorodithioate (IIa-1) to IIa, the phosphorodithioate triesters; by oxidation with iodine in the presence of alcohols to IIb, the phosphorothioate triesters; and by oxidation with aqueous iodine to IIb-1, the phosphorothioates.

The present novel compounds of general structure II having different heteroatoms containing substituents covalently linked to phosphorous can thus be prepared by processes A and B. In some cases where phosphorous is double bonded to sulfur and single bonded to nucleosides and to M to yield a dinucleoside phosphorodithioate, processes A and B can both be used to prepare the same compound IIa. For certain others such as IIc, where phosphorous is double bonded to oxygen and single bonded to nucleosides and to M, only process A can be used to produce this compound. Alternatively compounds IIb, IIb-1, IIe, and IIf having phosphorous double bonded to sulfur and single bonded to nucleosides and to X or G or T can only be synthesized by process B. It can therefore be seen that both processes of the present invention are required in order to synthesize all the compounds described by IIa-f. Process A also illustrates how compound Ia can be used to synthesize polynucleotides having phosphorodithioate and S-aryl or S-alkyl phosphorothioate triesters as internucleotide linkages. Process A when used to synthesize polynucleotides can be completed either on art form polymer support or in the absence of these supports.

Of course the nucleoside moiety of the present invention can include more than one nucleoside and may include a number of nucleosides condensed as having one or more phosphorous moieties (as shown in IIa-f) in combination with additional internucleotide phosphatediester linkages. These polynucleotides having a mixture of internucleotide linkages, and the presently described linkages as in IIa-f, are prepared using the novel processes comprising one aspect of the present invention in combination with preferably conventional phosphoramidite methodologies for synthesizing the other polynucleotide linkages (although other methods such as phosphate triester, phosphate diester, and H-phosphonate procedures can also be used to synthesize these additional linkages). These condensation steps are best carried out on polymer supports although nonpolymer support procedures can also be used.

The present invention is particularly useful in the chemical synthesis of any deoxyribonucleic acid (DNA) or ribonucleic acid (RNA) containing any deoxynucleotide, nucleotide, polynucleotide, or polydeoxynucleotide. These novel DNA or RNA compounds have analog substituents G, T, X or M plus sulfur double bonded to phosphorus at one or more internucleotide phosphorus containing linkages as found in DNA and RNA. The synthesis of compounds according to the general formula Ib can be represented by the following general reaction scheme C:

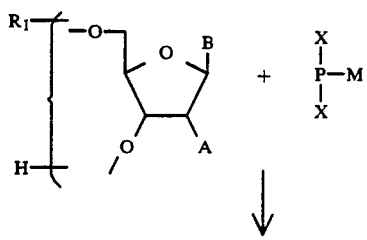

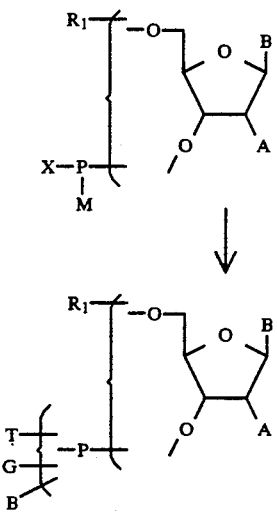

The preferred reaction scheme C is represented as follows:

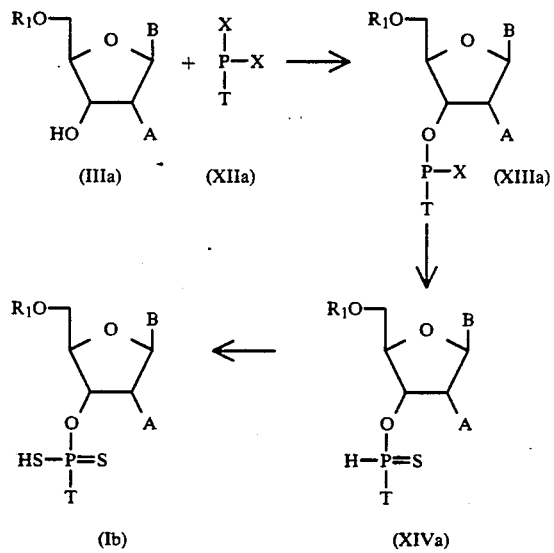

wherein $R_1$, B, A, and T are as previously described. Compounds Ib are those in which all compounds have phosphorus double bonded to sulfur and single bonded to a nucleoside, sulfur and T.

The process of scheme C involves synthesis of XIII and XIIIa from IIIa and XII or XIIa. Reaction of XIII or XIIIa with $H_2S$ and an activator such as tetrazole yields a novel compound, XIV, the nucleoside H-phosphonothioate, which can be chemically converted by oxidation with sulfur to Ib, the nucleoside phosphorodithioates.

The preferred novel compounds according to the present invention are those compounds of general formula Ia and IIa wherein for Ia, M is a substituent having sulfur bonded to phosphorus and to $R_5$ where $R_5$ is a heteroatom substituted or unsubstituted blocking group, A is H, $R_1$ is a trityl group, B is a nucleoside or deoxynucleoside base having art form blocking groups, and X is a secondary amino group; and for IIa, Z is sulfur double bonded to phosphorous, M is a substituent having sulfur single bonded to phosphorus and to $R_5$ where $R_5$ is a heteroatom substituted or unsubstituted blocking group, A is H, $R_1$ is a trityl group, B is a nucleoside or deoxynucleoside base having art-recognized blocking groups, and $R_3$ is H. Of course included in this preferred group of compounds is IIa-1 where M is the sulfhydryl group, SH.

The novel compound IIa-f of the present invention can be prepared as shown in scheme B from art-recognized starting materials such as VIIIa, a nucleoside 3'-phosphorodiamidite. The initial reaction is accomplished by dissolving the nucleoside in an organic solvent such as dioxane or tetrahydrofuran containing triethylamine to take up the liberated hydrochloric acid and adding a bis(dialkylamino) chlorophosphine. The resulting nucleoside phosphorodiamidite is reacted without isolation with a second nucleoside. The isolated product of this reaction is a dinucleoside dialkylamino phosphoramidite which can be reacted with hydrogen sulfide and tetrazole in an organic solvent such as acetonitrile to yield the dinucleoside H-phosphonothioate, IId. Further reaction of the isolated dinucleoside H-phosphonothioate with elementary sulfur in an organic solvent such as a mixture of toluene and lutidine yields the dinucleoside phosphorodithioate, IIa-1. Reaction of the dinucleoside phosphorodithioate with alkyl or aryl halide capable of alkylating thiols yields the sulfur protecting dinucleoside phosphorodithiosate triester, IIa. These novel compounds of the present invention can then be used to synthesize polynucleotides having phosphorodithioate moieties at selected phosphorus internucleotide linkages. This is possible by first removing the $R_3$ blocking group by conventional methods from preferably IIa and then reacting this with preferably an art-recognizing phosphorodiamidite which leads to the dinucleotide 3'-phosphoramidite for use as a synthon in preparing polynucleotides. Compounds IIa ($R_3$=H) can also be converted to dinucleotide 3'-phosphate, 3'-phosphate dieter, of 3'-H-phosphonate and synthesis of the polynucleotide then proceeds with these compounds either on silica-based polymer supports using recognized procedures or in reaction solutions free of polymer supports.

As a further embodiment of the invention, the dinucleoside phosphorodithioates, IIa, are preferably synthesized as shown in scheme A by forming the aralkylmercaptyl-bis(dialkylaminophosphine, IVa, and thereafter condensing this compound with the selected nucleoside using tetrazole as an activator in order to form a nucleoside S-(aralkyl)dialkylaminophosphoramidite. The nucleoside S-(aralkyl)dialkylaminophosphoramidite, Ia, can then be condensed with a second nucleoside using an activator in order to form an S-(aralkyl)dinucleoside phosphite, VIa, which after oxidation with elementary sulfur, yields IIa, the dinucleoside phosphorodithioate triester. This procedure obviates the requirement for dinucleoside phosphorodithioate triesters as synthons for preparing polynucleotides and is therefore preferred. Thus the nucleoside S-(aralkyl)-dialkylaminophosphoramidite and the art-recognized nucleoside phosphoramidities can be used in any desired sequence in concert with either elementary sulfur or aqueous iodine oxidation procedures, respectively, to yield polynucleotides having a selected combination of phosphorodithioate and phosphate internucleotide linkages.

The synthesis of aralkylmercaptyl-bis-dialkylamino phosphine is effected in an organic solvent solution whereby the bis(dialkylamino)-chlorophosphine is first synthesized and then further condensed with an aralkylmercaptan. The first step is reacting phosphorus trichloride in an organic solvent such as tetrahydrofuran or dioxane with a five-fold excess of the dialkylamine. The reaction proceeds smoothly at reflux in a dry atmosphere of nitrogen or argon. The solution of the product is separated from the precipitated hydrochloride salt of the added amine, and can be concentrated under reduced pressure to a solid. If the dialkylamine is at least as large as diisopropylamine, this solid can be recrystallized from chemically inert solvents such as pentane, hexane and heptane. Distillation of the bis(dialkylamino)chlorophosphine is also possible, especially for lower molecular weight compounds. The next step in the synthesis involves dissolving an aralkylmercaptan in an inert solvent such as ethyl ether, tetrahydrofuran or dioxane; adding an equivalent of sodium hydride in order to convert the mercaptan to the mercaptide; and finally adding the bis(dialkylamino)chlorophosphine to the reaction mixture. The S-aralkylmercaptyl-bis(dialkylamino)-phosphine is formed quantitatively over several hours at room temperature. Removal of sodium chloride followed by crystallization from solvents such as acetontrile or distillation afford the desired product.

Synthesis of internucleotide bonds containing phosphorodithioate linkages where aralkylmercaptyl-bis(dialkylamino)phosphine is used for this conversion requires activating agents which are proton donors. Thus, these phosphines are activated by acidic compounds through protonation which facilitates the formation of the desired internucleotide bonds containing initially a thiophosphite triester. The initial activation step involving the aralkylmercaptyl-bis(dialkylamino)phosphine requires acidic species, preferably mildly acidic, and includes tetrazole and 3-nitrotriazole. The resulting nucleoside aralkylmercaptyl-phosphoramidite is difficult to activate and requires more acidic species such as aromatic amine salts of strong acids, para-nitrophenyltetrazole, trifluoromethylphenytetrazole and trifluoromethyltetrazolide salts.

The mercaptyl moiety as part of the bis(dialkylamino) phosphine can vary considerably in structure. The criteria are that it facilitates activation of the mercaptyl-bis (dialkylamino) phosphine by acids, and that it can be easily removed after termination of the polynucleotide synthesis. Thus, the preferred mercaptans include benzyl and heteroatom substituted benzyl moieties, phenyl and heteroatom substituted phenyl moieties, and heteroatom substituted alkyl substituents such as $\beta$-cyanoethyl.

The bis(dialkylamino) moieties, as part of the aralkylmercaptyl-bis(dialkylamino) phosphine, are preferable substituents that stabilize both the phosphine and the nucleoside aralkylmercaptylphosphoramidite toward storage and synthesis. These dialkylamino groups should also preferably facilitate activation of the phosphine during the reactions leading to the formation of internucleotide bonds. These criteria are met most easily by substituents such as dimethylamino, diethylamino, diisopropylamino, dipropylamino, dibutylamino, dipentylamino, various isomeric alkyl groups, aralkyl groups, and heteroatom substituted cycloalkyl groups such as pyrrolidino and piperidino.

When the present novel compounds are used to form polynucleotides, they are preferably employed in combination with art recognized nucleoside phosphoramidites. Thus at sited where normal phosphate diester linkages are inserted into polynucleotides, art recognized procedures such as activation with tetrazole, oxidation with aqueous iodine, capping with acetic anhydride if synthesis is on art-recognized polymer supports, and detritylation with acid are used for synthesis. At the sites where phosphorodithioate linkages are to be incorporated into polynucleotides, a nucleoside, aralkylmercaptyl phosphoramidite is activated with aromatic amine salts, tetrazole, para-nitrophenyl tetrazole, trifluoromethylaryl tetrazole or similar reagents, and following coupling to the growing polynucleotide, the thiophosphite internucleotide linkage is oxidized, preferably with elementary sulfur to yield the dithioate. Other steps for utilizing the aralkylmercaptyl nucleoside phosphoramidite in the polynucleotide synthesis are the same as with art recognized nucleoside phosphoramidites. Dinucleoside phosphorodithioate triesters can also be used as synthons for polynucleotide synthesis. These novel compounds are prepared using the presently described novel processes. After conversion to preferably protected dinucleoside phosphorodithioate 3'-phosphoramidites, they can be activated with tetrazole and used directly as dinucleotide synthons via the normal art-recognized polynucleotide synthesis procedure, either preferably on polymer supports or in the solution phase in the absence of polymer supports.

Of course once the internucleotide bonds of the polynucleotide have been synthesized, which included both normal linkages and the phosphorodithioate linkages, the product can, if desirable, be freed of blocking groups. Thus the first step is treatment with preferably trialkylammonium thiophenolate to remove the aralkyl blocking group from the dithioate moiety and, if methyl groups are used to protect normal internucleotide linkages, the methyl group from these phosphate triesters. The remaining blocking groups on sugars, bases, or phosphorus, and also the linkage joining the polynucleotide to a support if the synthesis had been completed in this manner, can then be removed using art-recognized procedures such as hydrolysis with aqueous ammonia. If blocking groups on sulfur are used that are labile to reagents other than thiophenolate (e.g. trichloroethyl or β-cyanoethyl), then the deprotection protocol should be modified accordingly.

The following examples and procedures depicting the formation of the compounds according to the present invention are presented in order to provide a more complete understanding and illustration of the present invention.

EXAMPLE I

Preparation of thiophosphoramidites of the formula

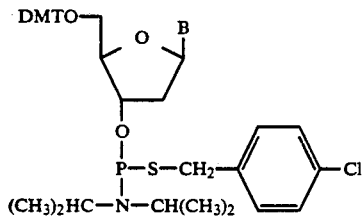

represented as Ia wherein
B=1-Thyminyl
B=1-(N-4-benzoylcytosinyl);
B=9-(N-6-benzoyladeninyl);
B=9-(N-2-isobutyrylguaninyl); and DMT=di-p-anisylphenylmethyl The synthesis of these compounds begins with the preparation of p-chlorobenzylmercaptyl-bis(diisopropylamino) phosphine. Phosphorus trichloride (0.5 mole, 68.665 g, 43.6 ml) was dissolved in 300 ml anhydrous tetrahydrofuran (THF). The PCl3 solution was cooled to −18° C. by a NaCl ice mixture. Diisopropylamine (2.5 mole, 252.983 g, 350.4 ml) was then added slowly via a dropping funnel. At first the reaction was violent and had to be carried out under vigorous stirring (mechanical stirrer) and cooling. After the reaction to the diisopropylamino dichlorophosphine was complete, the reaction mixture was refluxed for 12 hours to afford the desired product. After 12 hours the reaction mixture was cooled to room temperature and the diisopropylammonium chloride was removed by filtration through a Schlenk-fritt. After washing the salts with THF, the clear reaction mixture was refluxed again for 12 hours to afford the desired product as the only phosphorus containing material in the reaction mixture (31P-NMR delta 132.4 ppm). The newly formed diisopropylammonium chloride was removed by filtration and washed with anhydrous ether. The filtrate was evaporated under reduced pressure (rotary evaporator) to a yellowish solid which was recrystallized from hexanes to afford a colorless crystalline solid. This compound was air stable and moisture insensitive. Parachlorobenzylmercaptan (50 mmol, 7.93 g, 6.6 ml) was dissolved in anhydrous ether (300 ml) and an amount of a sodium hydride suspension in oil (50% NaH in oil) equivalent to 50 mmol (2.4 g) was added to the mercaptan solution. As the solution was stirred (magnetic stirrer), hydrogen evolved indicating the formation of sodium p-chlorobenzylmercaptide. After two hours, bis(diisopropylamino)chlorophosphine (50 mmol, 13.34 g) was added and the reaction mixture was stirred until gas evolution stopped (4 hours at room temperature). 31P-NMR of the reaction mixture indicated quantitative conversion of the chlorophosphine to the desired product without any side reactions (31P-NMR delta 91.4). The salt (sodium chloride) was removed by filtration through a Schlenk fritt and washed with anhydrous ether (50 ml). The colorless filtrate was evaporated to a white foam (p-chlorobenzylmercapty-bis(diisopropylamino) phosphine) which was dissolved in a minimum amount of hot acetonitrile (100 ml) and recrystallized from the same solvent to afford a white crystalline product.

The 5'-O-di-p-anisylphenylmethyl nucleoside (5 mmol) and p-chlorobenzylmercaptyl-bis(diisopropylamino)phosphine (6 mmol, 2.33 g) were suspended in dry acetonitrile (15 ml). Tetrazole (10 mmol, 0.69 g) was added and the reaction was stirred for 16 hours at room temperature. The initially present solids (phosphine and nucleoside) dissolved during the reaction time and a crystalline solid (diisopropylammonium tetrazolide) precipitates. After 16 hours, the reaction was quenched with pyridine (1 ml) and diluted into acid free ethyl-acetate (100 ml). The solution was extracted twice with an aqueous saturated solution of sodium bicarbonate and once with brine, successively.

The organic layer was dried over sodium sulfate. After removal of this salt, the solvent was evaporated in vacuo to afford a glass which was redissolved in a mixture of chloroform, ethylacetate and triethylamine (45:45:10, v/v/v) and chromatographed on silica gel with the same solvent. Column chromatography fractions containing the desired product were combined and the solvent evaporated in vacuo. The product was dissolved in toluene and precipitated into n-pentane. The nucleoside phosphorothioamidate was isolated after drying the precipitate in vacuo over $P_2O_5$/KOH (3.33 g, 80.1% yield).

31P-NMR delta 161.3 and 159.97 ppm (two diastereomers) with respect to external standard of H3PO4 for the thymidine derivative. 1H NMR delta 8.0 (N—H), 7.59 and 7.58 (2×d, JHH=1.2 Hz), 7.42-7.19 (m), 6.83 (d, JHH=8.7 Hz), 6.37 (q, H1'), 4.65-4.58 (m,H3'), 2.05-1.83 (m, H6'), 3.80-3.61 (m, CH2 of p-chlorobenzyl), 3.78 (s, H6), 3.48-3.29 (m, H5'), 2.45-2.24 (m, H2), 1.44 (Ch3-T), 1.17-1.04 (m, CH3 of isopropyl).

EXAMPLE II

Synthesis of dinucleoside phosphorodithioate triesters of the formula:

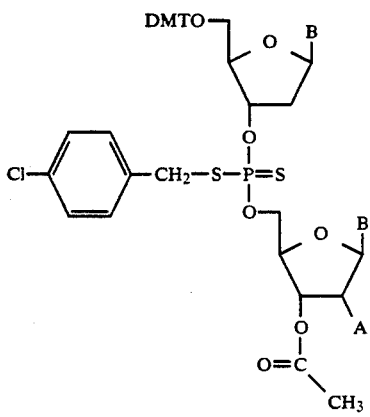

represented as IIa wherein
B=1-Thyminyl;
B=1-(N-4-benzoylcytosinyl);
B=9-(N-6-benzoyladeninyl);
B=9-(N-2-isobutyrylguaninyl); and
DMT=di-p-anisylphenymethyl 5'-I-di-p-anisylphenymethylthymidine-3'-S-(p-chlorobenzyl) diisopropylaminophosphoramidite (compound Ia) (0.2 mmol, 166.3 mg) and 3'-O-acetylthymidine (0.2 mmol, 56,8 mg) were dissolved in anhydrous dimethylformamide (2 ml). p-Nitrophenyltetrazole (1 mmol, 191.2 mg) was next added to this solution. After 15 minutes, the reaction to the dinucleoside thiophosphite was quenched with sulfur (1 mmole, 32 mg), The reaction mixture was then diluted with ethylacetate (50 ml) and the sulfur removed by filtration through a cotton plug. After removal of the solvents in high vacuo, the desired product was dissolved in ethylacetate (10 ml) and extracted twice with aqueous saturated solution of sodium bicarbonate and once with brine, successively, The organic layer was dried over sodium sulfate. After removal of the salt, the product was chromatographed on silica with a mixture of 1.1.1-trichloroethane and methanol (92.5:7.5, v/v). The product fraction were combined and the solvent removed in vacuo. The dinucleoside phosphorodithioate was dissolved in Toluene and precipitated into n-pentane (31P-NMR delta 97.8, 96.2 with respect to 85% H3PO4 as an external standard). FAB-mass spectrum, 1047 (M−), 921 (-p-chlorobenzyl), 743 (-DMT), 619 (-DMT and p-chlorobenzyl), 519 (3'-O-acetylthymidine 5'-O-p-chlorobenzylphosphorodithioate), 395 (3'-O-acetylthymidine 5'-O-phosphorodithioate).

The p-chlorobenzyl group was removed from the phosphorodithioate triester with a mixture of dioxane:-triethylamine:thiophenol (2:2:1, v/v/v) within 1.5 hours at room temperature.

EXAMPLE III

Synthesis of dinucleoside H-phosphonothioate of the formula:

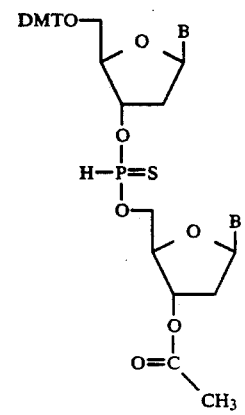

represented as IId wherein
B=1-Thyminyl;
B=1-(N-4-benzoylcytosinyl);
B=9-(N-6-benzoyladeninyl);
B=9-(N-2-isobutyrylguaninyl); and
DMT=di-p-anisylphenylmethyl The first step was condensation of 5'-O-dimethoxytritylthymidine with bis(diisopropylamino)-chlorophosphine in dioxane containing triethylamino. The resulting phosphorodiamidite was reacted without isolation with 3'-O-acetylthymidine to yield a homogeneous dinucleoside amidite in 62% yield after silica gel chromatography (5% triethylamine in ethylacetate). Synthesis of the dinucleoside H-phosphonothioate processed by dissolving the dinucleoside phosphoroamidite (470 mg. 0.5 mmol) in acteonitrile (5 ml), bubbling H2S through the solution for 1 min, adding tetrazole (35 mg, 0.5 mmol in 1 ml acetonitrile). And finally stirring the sealed reaction flasks for 16 hours. The reaction mixture was concentrated to a gum on a rotary evaporator, redissolved in ethylacetate (50 ml) and extracted twice with 2M triethylammonium bicarbonate (pH 7.4, 20 ml each). After concentrating in vacuo to a gum, the product as dissolved in dichloromethane (5 ml) and isolated by precipitation into pentane (400 mg 90%). FAB+ mass spectrum, 527 (anhydro DMT dt); FAB-mass spectrum, 890 (M−), 623 (DMT dt-3'-PHO2-), 363 (M-527, 5'-PHO2--dT-3'-OAc); 31P-NMR delta 71.7 and 70.7 (1JHP=673.8 Hz and 676.3 Hz); 1 H NMR delta 7.81 and 7.80 (P-H, 1JHP=671.4 Hz and 676.7 Hz), 7.55 and 7.53 (s, H6), 7.37-7.20 (m, aromatic), 6.82 (d, J=8.8 Hz, DMT), 6.49 and 6.26 (m, H1'), 5.49 and 5.25 (m, H3'), 4.35 (m, H4'), 4.19 (m, H5'), 4.07 (m, H4'), 3.76 (s, MeO-DMT), 3.42 (m, H5'), 2.54-2.32 (m, H2'), 2.08 and 2.07 (2×s, CH3-acetyl) 1.90 (m, CH3-T), 1.43 (s, CH3-T). Rf=0.35 and 0.28 (methanol/dichloromethane, 1:9, v/v).

EXAMPLE IV

Synthesis of a dinucleoside phosphorodithioate of the formula:

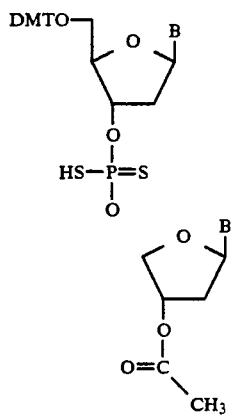

represented as IIa-1 wherein
B=1-Thyminyl;
B=1-(N-4-benzoylcytosinyl);
B=9-(N-6-benzoyladeninyl);
B=9-(N-2-isobutyrylguaninyl); and
DMT=di-p-anisyphenylmethyl Dithymidine phosphorodithioate was synthesized by stirring the dinucleoside H-phosphonothioate (104 mg, 0.1 mmol in 1 ml dichloromethane) with elementary sulfur (1 mmol in 2 ml toluene: 2, 6-lutidine, 19:1, v/v) for 0.5 hours. Purification via silica gel column chromatography (0–12% methanol in dichloromethane and 0.5% triethylamine) afforded 70% isolated yield. FAB+ mass spectrum, 303 (DMT+); FAB-mass spectrum, 921 (M−), 395 (5'-PSO$_2$--dt-3'-OAc); 31P-NMR delta 112.7; 1H NMR delta 8.12 (s, NH), 7.90 and 7.60 (2×s, H6), 7.40–7.24 (m, aromatic), 6.80 (d, JHP=8.8 Hz, DMT), 6.43 (m, H1'), 5.46–5.36 (m, H3'), 4.40 (m, H4'), 4.16 (m, H5'), 3.76 (s, Meo-DMT), 3.52 (m, H5'), 2.28 (m, H2'). 2.05 (CH$_3$-acetyl), 1.97 (CH$_3$-T), 1.58 (s, CH$_3$-T). Rf=0.14 (methanol/dichloromethane, 1:9, v/v).

The dinucleoside phosphorodithioate was deprotected by standard procedures and isolated in 86% yield after ether extractions (3×), Sephadex ™ G10 gel filtration (H2O), and lyophilization as the ammonium salt. FAB+ mass spectrum, 579 (M); 31P-NMR delta (D2O) 113.3; 1H NMR delta 7.60 and 7.46 (2×s, H6), 6.11 and 5.99 (m, H1'), 5.17 (m, H3'), 4.85 (m, H3'), 4.15 (m, H4'), 4.03 and 3.62 (m, H5'), 2.21 (m, H2'), 1.88 (m, CH3-T). Rf=0.25 (methanol/triethylamine/chloroform, 15:1:84, v/v/v). When the dinucleoside phosphorodithioate was phosphorylated with T4-polynucleotide kinase and [gamma-32P] ATP, the rate of kination was approximately one-half that of unmodified 3'-5' dithymidine phosphate under identical conditions. Further testing with snake venom phosphodiesterase (Crotalus adamanteus venom, Sigma) indicated that the phosphorodithioate was stable using conditions where the natural dinucleotide was completely hydrolyzed (assayed by reverse phase HPLC). This compound was also observed to be stable to conc. ammonium hydroxide at 55° C. (16 h) as no degradation or isomerization was observed ($^{31}$P-NMR, thin layer chromatography).

EXAMPLE V

Synthesis of a dinucleoside phophorodithioate 3'-phosphoramidite of the formula:

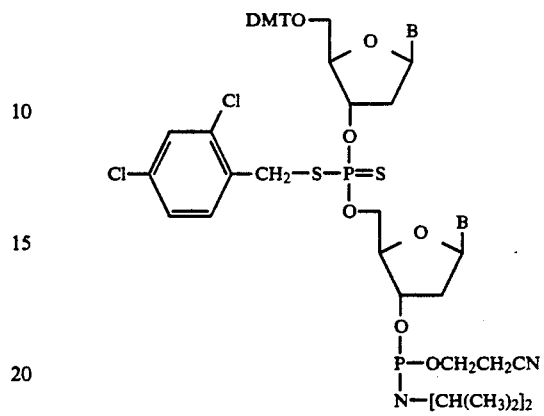

represented as XVa wherein
B=1-Thyminyl;
B=1-(N-4-benzoylcytosinyl);
B=9-(N-6-benzoyladeninyl);
B=9-(N-2-isobutyrylguaninyl); and
DMT=di-p-anisylphenylmethyl In order to introduce the phosphorodithioate linkage into oligonucleotides, a protection/deprotection scheme for the phosphorodithioate internucleotide linkage was developed. Thus, the dinucleoside phosphorodithioate, IIa-1, (57 mg, 0.06 mmol) was alkylated with alpha,2,4-trichlorotoluene (50 μl, 1 h, 55 C) in acetonitrile to yield the dinucleoside phosphorodithioate triester quantitatively. Further testing revealed that it was completely stable to reagents used in DNA synthesis (1% trifluoroacetic acid in dichloromethane and iodine in aqueous lutidine/THF) and that the phosphorodithioate triester was specifically S-dealkylated by treatment with thiophenolate (thiophenol:triethylamine:dioxane, 1:1:2, v/v/v. t$\frac{1}{2}$=3 min at room temperature). FAB+ mass spectrum, 527 (anhydro DMT dt); FAB− mass spectrum, 923 (M+1-dichlorobenzyl), 813 (DMT dt-3'-PSOS-dcb), 553 (5'-PSOS-dcb-dT-3"OAc); 31P-NMR (CH$_3$CN, ext. lock) delta 94.4 and 93.7, 1H NMR delta 7.55 and 7.52 (2×s, H6), 7.37–7.23 (m, aromatic) 681 (d, J+4.6 Hz, DMT), 634 and 6.28 (m, H1'), 5.38 and 5.01 (m, H3'), 4.24–4.08 (m, CH$_2$-benzyl, H5'+H4'), 3.76 (s, MeO-DMT), 3.42 (m, H5'), 2.39 (m, H2'), 2.08 (s, CH$_3$-acetyl), 1.89 and 1.87 (2×s, CH$_3$-T). 1.43 and 1.42 (2×s, CH$_3$-T). Rf=0.74 (methanol/triethylamine/chloroform, 15:1:84, v/v/v.

Conversion of synthon useful for DNA synthesis was a two step process. The dinucleoside phosphorodithioate triester was first deacylated (the 3' acetyl group) using 0.15 M tert-butylamine in methanol (0° C., 10 h) and purified by silica gel chromatography to yield IIa (R$_3$=H). Less than 5% cleavage of the internucleotide linkage (31P NMR, TLC) was observed. The deacylated compound was then reacted with bis(diisopropylamino)-2-cyanoethoxy phosphine (1.5 eq) in the presence of tetrazole (1 eq, 1 h at room temperature) to yield the dinucleoside phosphorodithioate triester as the 3'-phosphoramidite in 76% yield. 31P-NMR delta 149.4, 149.4, 148.9 and 97.2, 95.7, 95.5. IH NMR delta 7.56 (s, H6), 7.33–7.27 (m, aromatic), 6.84 (d, J=8.5

Hz), DMT), 6.39–6.29 (m, H1'), 5.44 (m, H3'), 3.79 (s, MeO-DMT), 1.90 (s, CH$_3$-T), 1.45 (s, CH$_3$-T), 1.18 (d, J=6.6 Hz, CH$_3$-iPr). Rf=0.29 and 0.17 (chloroform.ethylaceate.triethylamine, 45:45:10, v/v/v). The resulting dinucleotide phosphoramidite, XVa, has been used successfully in combination with unmodified mononucleoside phosphoramidites for the synthesis of a 26-mer DNA fragment containing the phosphorodithioate linkage between position 8-9 (98.2% coupling efficiency). The synthesis was completed on silica based polymeric supports and phosphoramidite coupling methodologies U.S. Pat. Nos. 4,458,066 and 4,415,732). The oligodeoxynucleotide had the following sequence where the one phosphorodithioate linkage is marked x instead of p. d(TpGpTpGpGpApApTxTpGpTpGpApGpCpGpGpApTpApApCpApAptpt).

EXAMPLE VI

Synthesis of dinucleoside thioamidates, thiotriester, and thioate of the formulae:

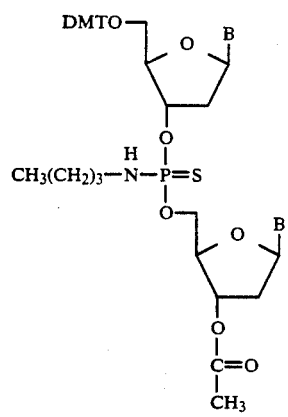

(IIf)

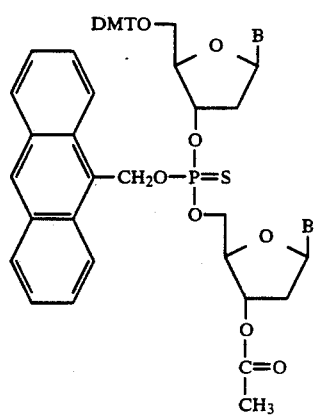

(IIb)

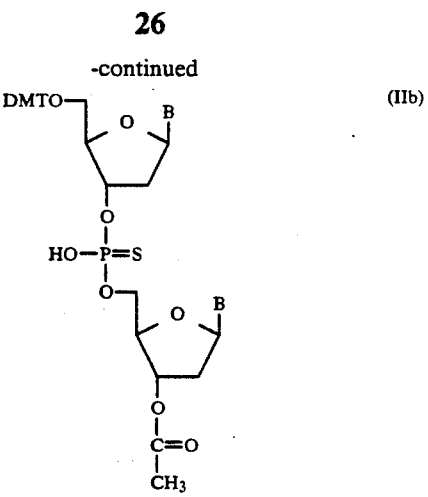

(IIb)

represented as IIb and IIf wherein
B=1-Thyminyl;
B=1-(N-4-benzoylcytosinyl);
B=9-(N-6-benzoyladeninyl);
B=9-(N-2-isobutyrylguaninyl); and
DMT=di-p-anisylphenylmethyl The dinucleoside H-phosphonothioate was also found to be useful as a versatile synthon for preparing several analogs rapidly (5 min) in quantitative yield ($^{31}$P-NMR). Thus when oxidized with iodine/n-butylamine the phosphorothioamidate (IIf) was isolated in 92% yield. FAB− mass spectrum, 961 (M-), 695 (DMT dt-3'-POSNHBU), 434 (5'-POSNHBU-dt-3'-OAc); $^{31}$P-NMR delta 74.4 and 74.0; 1H NMR delta 8.36 and 8.34 (2×s, NH), 7.59 and 7.56 (2×s, H'), 7.44–7.24 (m, aromatic), 6.82 (d, J=8.7 Hz, DMT), 6.41 and 6.28 (m, H1'), 5.28 and 5.23 (m, H3'), 4.21 and 4.13 (m, H4'(2×)-H5'), 3.77 (s, MeO-DMT), 3.43 (m, H5'), 2.94 (m, CH$_2$—N), 2.41 (m, H2'), 2.09 and 2.07 (2×s, CH$_3$-acetyl), 1.93 and 1.88 (2×s, CH$_3$-T), 1.42 (s, CH3-T), 1.39–1.23 (m, CH2), 0.90 and 0.83 (2×t, J=7.2 Hz and 7.1 Hz, CH$_3$). Rf=0.56 (methanol/dichloromethane, 1:9, v/v).

The dinucleoside H-phosphonothioate was converted quantitatively to a phosphorothioate triester by oxidation with iodine and 9-anthracenyl methanol (10 equivalents) under anhydrous conditions (IIb). FAB+ mass spectrum, 527 (anhydro DMT dt); FAB− mass spectrum, 906 (m-anthracenylmethyl), 639 (DMT dt-3'-PSO$_2$-), 379 (5'-PSO$_2$-dt-3'-OAc). $^{31}$P-NMR delta 51.7 and 51.0. Rf=0.41 (methanol/dichloromethane, 1:9, v/v).

Treatment of the dinucleoside H-phosphonothioate with an aqueous solution of iodine and pyridine using art form conditions gave the dinucleoside phosphorothioate (IIb) in 87% yield. FAB− mass spectrum, 906 (M-), 603 (M-DMT), 379 (5'-PSO$_2$-dt-3'-OAc). $^{31}$P-NMR delta 60.2 and 60.0.

EXAMPLE VII

Synthesis of nucleoside 3'-phosphorodithioate of the formulae:

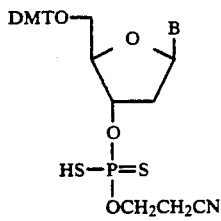

represented as Ib wherein
B=1-Thyminyl;
B=1-(N-4-benzoylcytosinyl);
B=9-(N-6-benzoyladeninyl);
B=9-(N-2-isobutyrylguaninyl); and
DMT=di-p-anisylphenylmethyl 3'-O-(Diisopropylamino)-2-cyanoethyphosphino-5'-O-(di-p-methoxytrityl) thymidine (27.7 mg, 0.04 mmol) was prepared by art form methods (M. H. Caruthers and S. L. Beacage U.S. Pat. No. 4,415,732) and then dissolved in anhydrous acetonitrile (440 μl). Hydrogen sulfide was bubbled through for 1 min and tetrazole (7.0 mg in 200 μl CH$_3$CN, 0.1 mmol) was added. After 10 min $^{31}$P-NMH spectroscopy showed quantitative conversion to the diastereomers (delta 70.9 and 70.2 ppm, 1JPH=675 Hz) of the nucleoside H-phosphorodithioate. $^{31}$P-NMR (CH$_3$CN) delta 114.0 ppm. FAB− mass spectrum, 708 (M-), 182 (M-DMT dt+0). 1H NMR (CDCl$_3$) 7.53 (s, H6), 7.35–6.81 (m, aromatic), 6.15 (t, H1' J=6.4 Hz), 5.12 (m, H3'), 4.20 (m, CH$_2$O-P), 2.77 (t, CH$_2$CN, J=6.2 Hz), 2.56–2.44 (m, H2'), 1.91 (s, CH$_3$—T).

Protected nucleoside 3'-phosphorodithioate was dissolved in 80% aqueous acetic acid (4 ml) and left for 30 min at room temperature. The reaction mixture was then diluted with water (4 ml) and extracted 3 timed with ether (5 ml). The water phase was evaporated to an oil followed by a co-evaporation with water (5 ml). The oil was redissolved in 25% aqueous ammonia and incubated at 55° C. for 16 h. The mixture was re-evaporated and lyophilized with water to yield the nucleoside 3'-phosphorodithioate. FAB− mass spectrum, 338 (M-). FAB+ mass spectrum, 338 (dt-P+SH=S).

EXAMPLE VIII

Synthesis of nucleoside 5'-phosphorodithioate of the formula:

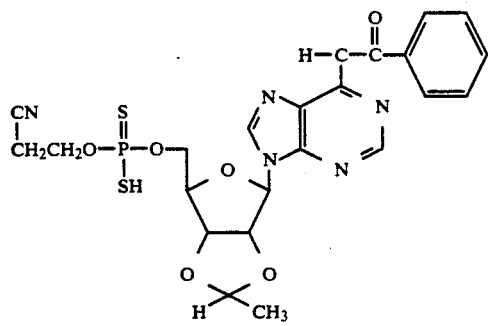

represented as Ib wherein
B=1-Thyminyl
B=1-(N-4-benzoylcytosinyl);
B=9-(N-6-benzoyladeninyl);
B=9-(N-2-isobutyrylguaninyl); and
DMT=di-p-anisylphenylmethyl.

A solution of N6-benzoyl-2-3-methoxymethylideneadenosine (413 mg, 1.1 mmol) in anhydrous CHCl$_3$ (5 ml and tetrazole (76 mg, 1.1 mmol, in CH$_3$CN (2.2 m.)) was added 2-cyanoethyl-N,N,N',N'-tetraisopropyl phosphorodiamidite (345 mg, 1.1 mmol) and stirred at room temperature for 20 min. Precipitation of diisopropyl ammonium tetrazolide appeared after ½ min. The reaction mixture was diluted with CH$_2$CL$_2$ (50 ml) and extracted with NaHCO$_3$ (5% w/v, 50 ml), back-extracted with CH$_2$CL$_2$ (25 ml), the organic phase dried over Na$_2$SO$_4$, filtered and evaporated to dryness in vacuo. $^{31}$P-NMR analysis (CH$_3$CN) showed delta 147.9 ppm. Crude product (0.71 g) was dissolved in anhydrous CH$_3$CN (5 ml) and bubbled with hydrogen sulfide for 1 min. The reaction mixture was sealed and after 10 min a precipitate of diisopropyl ammonium tetrazolide appeared $^{31}$P-NMR (CH$_3$CN) delta 72.2 and 71.8 ppm, 1 JPH=669 Hz). The reaction mixture was evaporated to an oil in vacuo, redissolved in ethylacetate (50 ml), extracted with TEAB (1M, pH=7.4, 50 ml), and back-extracted with ethylacetate (50 ml). The combined organic phases were dried over Na$_2$SO$_4$, filtered, evaporated, and the oil was redissolved in CH$_2$Cl$_2$ (5 ml.) Excess elementary sulfur (80 mg, 2.5 mmol, in 5 ml toluene/2,6-lutidine, 19:1, v/v) was added. Stirring at room temperature for 1 h gave the phosphorodithioate product. $^{31}$P-NMR (CH$_3$CN) delta 114.4 and 114.3. Rf (silica)=0.34 in CH$_2$Cl$_2$ (9:1, v/v).

In addition to those compounds described above, a second aspect of the present invention provides novel and useful nucleotides and polynucleotides having other structure modifications at the phosphorus atom and to the process leading to the synthesis of these compounds. More specifically, the invention described procedures for synthesizing polynucleotide phosphorodithioate, H-phosphonothioate, phosphorothioate and phosphorothioamidate compounds from nucleosid-3'-yl phosphorodiamite and compounds from nucleosid-3'-yl phosphorodiamidite and nucleosid-3'-yl phosphorothioamidite synthons. These procedures are especially useful for preparing high molecular weight polynucleotides having these modifications or high molecular weight polynucleotides having these modifications in any combination or in combination with natural internucleotide linkages. The invention therefore provides procedures for preparing polynucleotide phosphorodithioate, H-phosphonothioate, phosphorothioate, alkylphosophonothioate and phosphorothioamidate compounds from nucleosid-3'-yl hydrogen phosphonodithioate, nucleosid-3'-yl-S-aralkylphosphorodithioate and nucleosid 3'-methylphosphonothioate synthons. These additional novel procedures of the invention are especially useful for preparing polynucleotide phosphorodithioate, polynucleotide phosphorothioate, polynucleotide methylphosphonothioate and polynucleotide phosphorothioamidate compounds either exclusively or in any combination including combinations with natural internucleotide linkages where large quantities of polynucleotides are required for various uses. The polynucleotide phosphorodithioate compounds synthesized with the nucleosid-3'-yl hydrogenphosphonodithioate and nucleosid-3'-yl-S-aralkyl phosphorodithioate synthons also appear to have less contamination of the phosphorothioate side-product.

In general, the compounds according to this second aspect of the present invention may be represented specifically than previously described (for example, compound XXI is more specific than compound Ia described earlier) by the following general formulae XXI to XXIX:

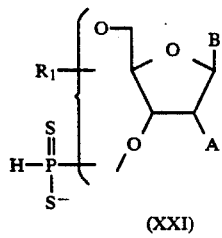
(XXI)

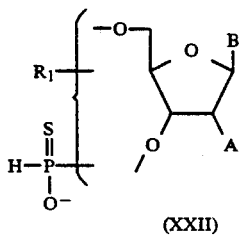
(XXII)

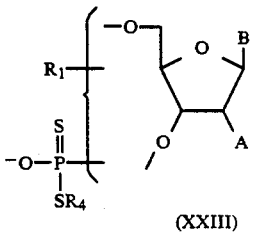
(XXIII)

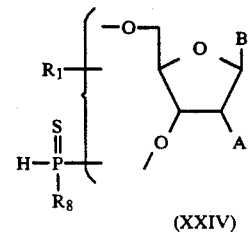
(XXIV)

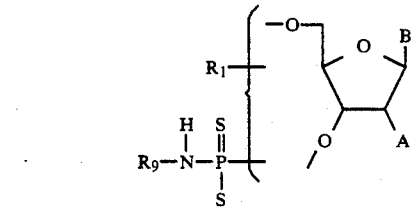
(XXV)

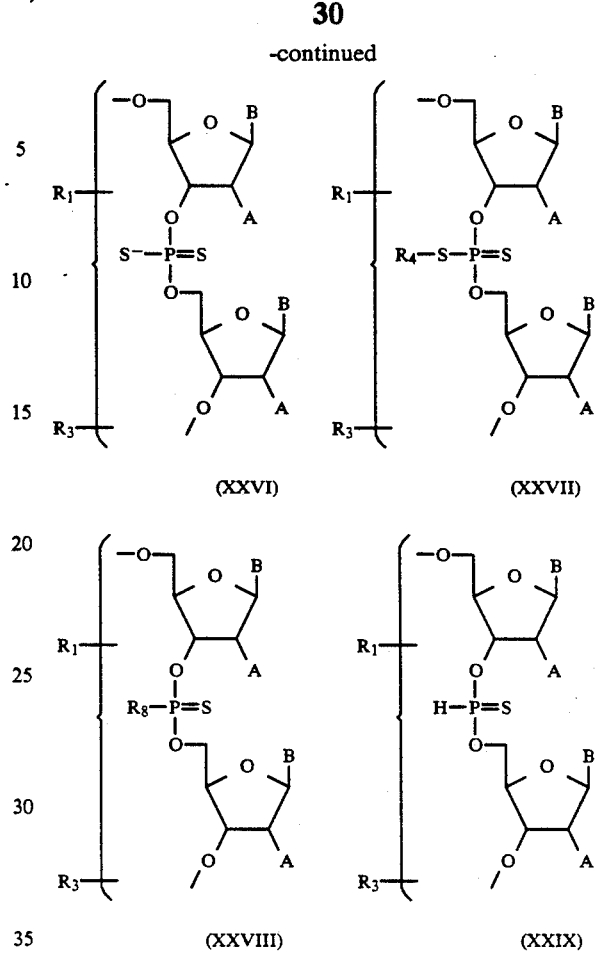

The compounds of general formula XXI, XXII, XXIII and XXIV are useful for the synthesis of polynucleotides containing phosphorodithioate, phosphorothioamidate, alkyl or aryl phosphonothioate and phosphorothioate internucleotide linkages which are useful for various biological applications. These compounds are also useful for various biological applications.

In general, one reaction scheme for the synthesis of compounds XXI, XXII, XXV, XXVI, XXVII and XXIX are shown in the following overview:

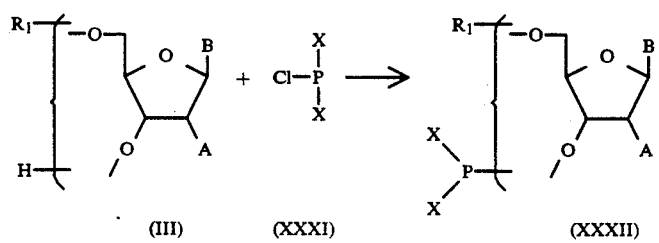

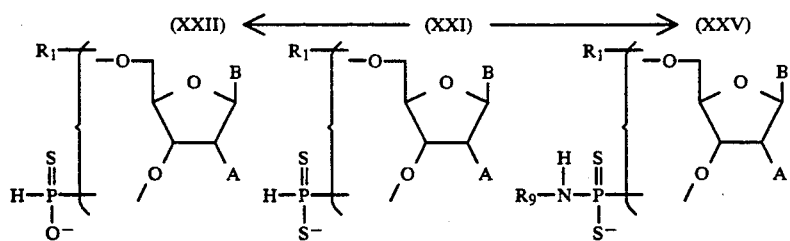
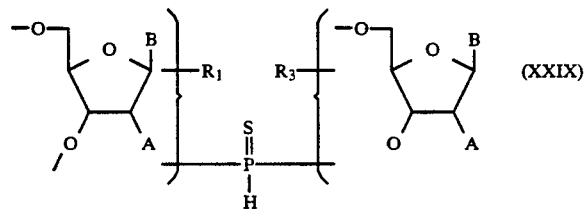
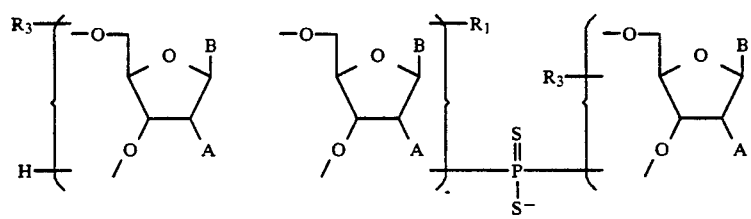
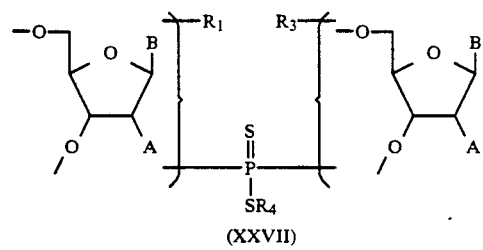
The preferred reaction scheme for synthesizing compounds XXI, XXII, XXV, XXVI, XXVII and XXIX are shown in the following overview:
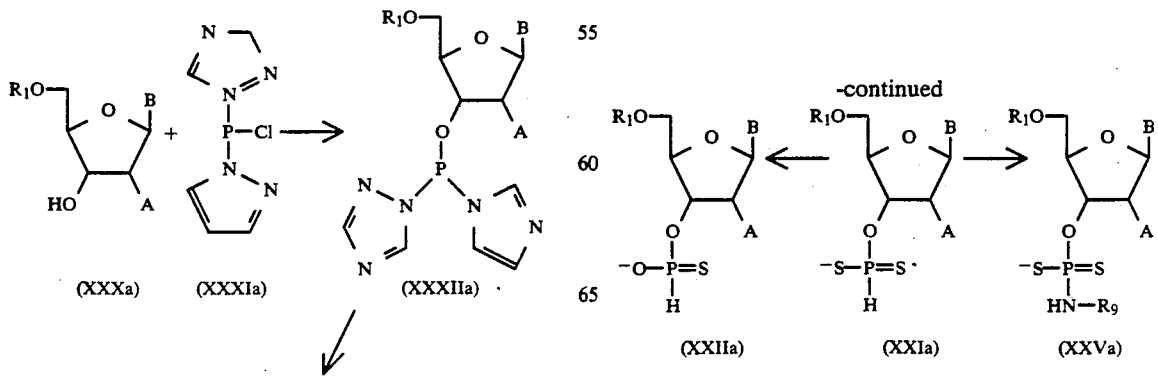

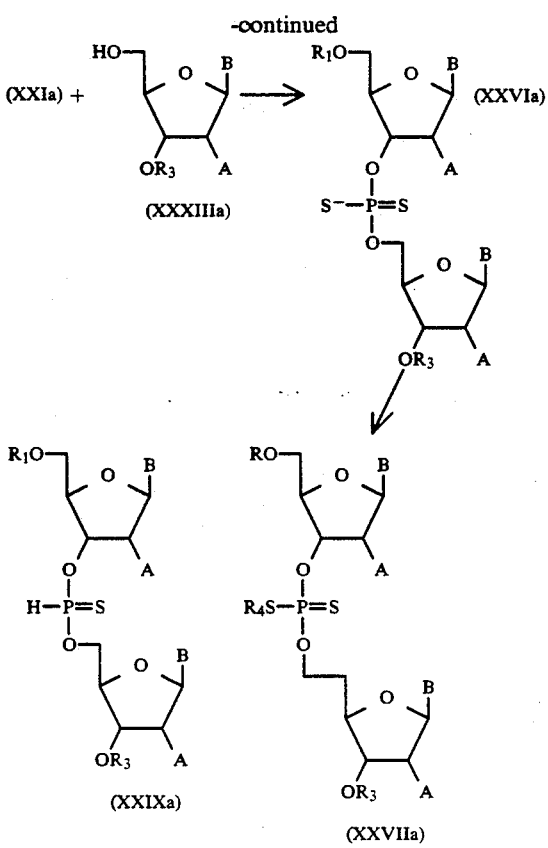

The process of the generalized reaction scheme involves first the synthesis of XXIa and the conversion of this novel compound to various mononucleotides and oligonucleotides having modified chemical structures. The synthesis of XXIa proceeds by reacting XXXa with preferably bis(triazoyl)chlorophosphine, compound XXXIa, followed by a treatment with H$_2$S for five minutes. Various other bis-aminophosphines such as tetrazoyl, imidazoyl, diisopropylamino, dimethylamino, diethylamino, morpholino, piperidino and pyrrolidono derivatives are additional examples of amino groups that can be used. After purging with an inert gas to remove H$_2$S, compound XXIa can be isolated by purification and precipitation. Compound XXIa can then be converted via novel processes to XXIIa. Thus, when compound XXIA is treated with one equivalent each of water and dicyclohexylcarbodiimide or N-methyl-2-chloropyridinium iodide in pyridine for 30 minutes, the nucleoside 3′-hydrogenphosphonothioate forms in essentially quantitative yield. Formation of compound XXIXa via a similar reaction was possible by treatment of compound XXIa with compound XXXIIIa and N-methyl-2-chloropyridinium iodide. After 15 minutes reaction time, compound XXIXa can be isolated by purification and precipitation from n-pentane. Thus, compound XXIa can be used to prepare dinucleoside hydrogenphosphonothioates. These novel compounds XXIa are not as reactive as the nucleoside diamidites and not as unstable, but reacts readily with unblocked 3′-OH or 5′-OH of nucleosides under normal reaction conditions. The novel nucleoside hydrogenphosphonodithioates are stable under normal laboratory conditions to hydolysis and air oxidation and may be stored as dry, stable powders. Therefore, the novel compounds are more easily employed in the process of forming internucleotide H-phosphonothioate bonds. The resulting compound XXIXa can then be used to form nucleoside phosphorodithioates, dinucleoside phosphorothioamidates, and dinucleoside phosphorothioates.

The novel compound XXIa may be used to form novel mononucleotide phosphorodithioamidates and dinucleoside phosphorodithioates via a novel oxidative process. The synthesis of compound XXVa, a mononucleotide phosphorodithioamidate, proceeds by treating a pyridine solution of compound XXIa with 2-aminoanthracene and iodine to yield compound XXVa which may be isolated after purification by precipitation from n-pentane. When XXIa and XXXIIIa in pyridine were treated with one equivalent iodine, the dinucleoside phosphorodithioate, compound XXVIa was the only detectable product. After addition of sodium bisulfite to oxidize any excess iodine and filtration to remove salts, compound XXVIa may be isolated by purification and precipitation from n-pentane. Thus, compound XXIa can be used to prepare XXVIa, the dinucleoside phosphorodithioate. For preparation of dinucleoside phosphorodithioates, compound XXVIa, the condensation of XXIa with XXXIIIa may be monitored by decolorization of the iodine solution. This is an especially attractive feature as the persistence of the light brown color of excess iodine indicates when the coupling is complete. Furthermore, this novel method also appears to be relatively free of reactions which lead to significant quantities of phosphorothioates as side products. This is because contaminating oxygen does not interfere with the activation process and elemental sulfur, which is difficult to solubilize and is a rather poor oxidant of P(III) compounds, is not part of the sulfurization reactions.

The resulting novel dinucleoside phosphorodithioate can then be reacted with various alkylating agents to yield XXVIIa, and this compound may then be incorporated into polynucleotides.

In addition to this first novel process, a second reaction scheme was also discovered for the purpose of synthesizing compounds XXXVIII and XXVII, the completely protected dinucleoside phosphorodithioate triester. This second scheme is as follows:

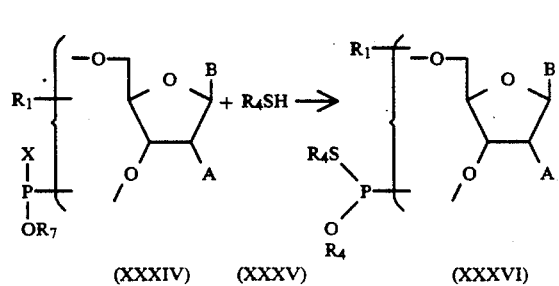

-continued

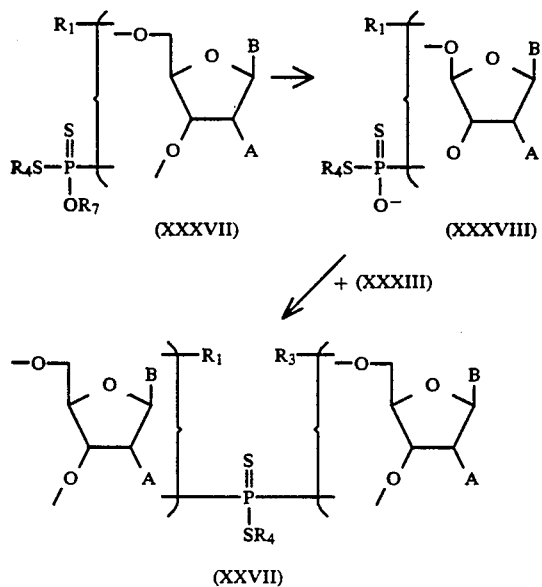

The preferred reaction scheme is as follows:

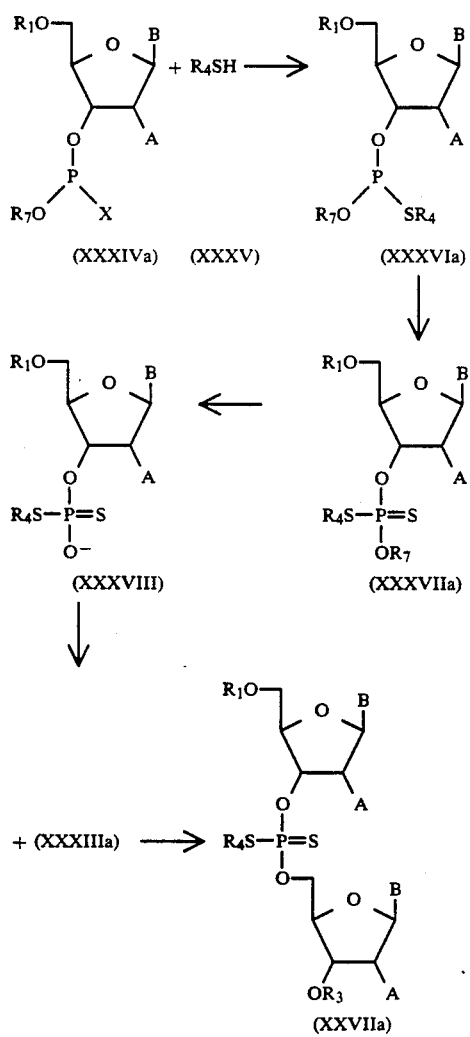

Preferably, $R_1$, $R_4$, and $R_7$ may be removable as blocking groups under different chemical conditions so that each can be selectively eliminated in the presence of the other. One such preferable combination of conditions would be $R_1$ removed with acid (as in the case of di-p-methoxytrityl), $R_7$ removed by a base (as in the case of $\beta$-cyanoethyl), and $R_4$ removed by thiophenol (as in the case of 2,4-dichlorobenzyl). Of course all other "blocking groups" according to the invention may also be selected so that each can be selectively eliminated in the presence of the others. Using these combinations of blocking groups, XXVII can be extended to form polynucleotides simply by removing either $R_1$ or $R_3$ preferentially followed by the chemistry outlined in the scheme immediately above.

The process of the scheme above involves the condensation of nucleoside phosphoramidites such as XXXIVa according to the process in U.S. Pat. No. 4,415,732 to yield XXXVIa. Reaction of XXXVIa without isolation with sulfur yields XXXVIIa which can them be converted to XXXVIIIa with triethylamine under anhydrous conditions. The triethylammonium salts of XXXVIIIa may then be stored as a solid. Of course, other bases that preferentially remove the $R_7$ protecting group in the presence of $R_4$ may also be used. Reaction of XXXVIIIa with XXXIIIa in the presence of triisopropylbenzenesulfonyl chloride then yields XXVIIa, the completely protected dinucleoside phosphorodithioate. Of course, other activating agents such as mesitylenesulfonyl chloride and tetrazolide can be used to synthesize XXVIIa. Compound XXVIIa may then be further extended to synthesize larger polynucleotides by removing $R_1$ from XXVIIa with acid and condensing the resulting compound with XXXVIIIa using triisopropylbenzenesulfonyl chloride or tetrazolide as a condensing agent to yield a trinucleotide with two phosphorodithioate linkages. Alternatively, XXVIIa may be treated with a base to remove $R_3$ and then converted to the dinucleoside 3'-phosphoramidite analogous to XXXIVa, using the known conditions in U.S. Pat. No. 4,415,732, which can subsequently be converted as in the scheme immediately above to a dinucleoside-3'-yl-S-aralkylphosphorodithioate analogous to XXXVIIIa. This compound may then be condensed with XXVIIa, where $R_1$ has been removed with acid, using triisopropylbenzenesulfonyl chloride to yield a tetranucleotide having three phosphorodithioate linkages. These polynucleotides may then be further extended in a similar manner to form longer polynucleotides having phosphorodithioate linkages or by using nucleoside 3'-phosphate diesters to polynucleotides having both phosphorodithioate and phosphate internucleotide linkages.

A third novel reaction scheme for the purpose of synthesizing novel compound XXIV which may be used to synthesize compounds XXIV and XXVIII is depicted below:

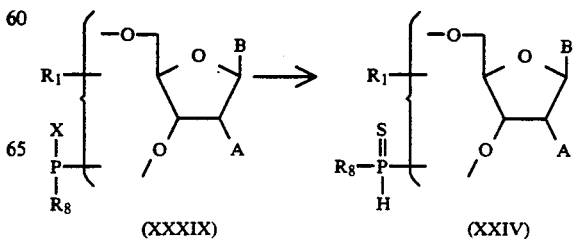

-continued

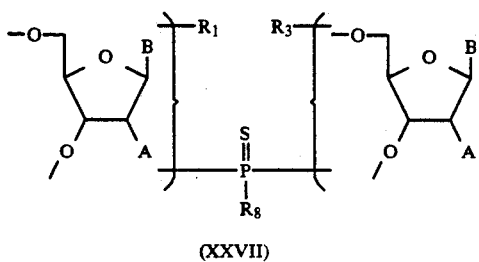

(XXVII)

The preferred reaction scheme is represented as:

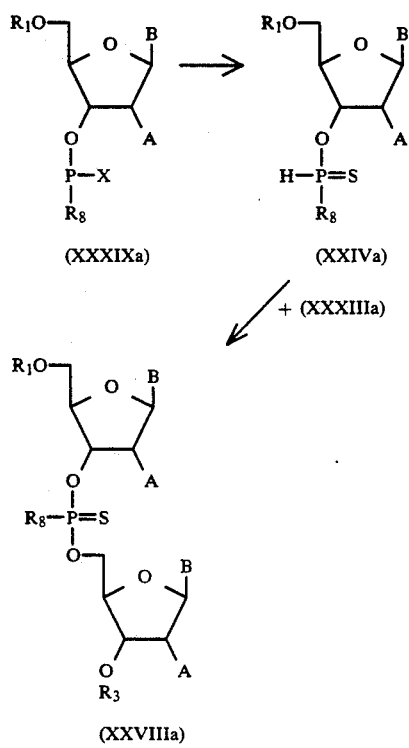

wherein $R_8$ is a heteroatom substituted or unsubstituted alkyl, aryl, aralkly, cycloalkyl, cycloalkylalkyl, alkenyl, cycloalkenyl, aralkenyl, alkynyl, aralkynyl, or cycloalkynyl group.

The process of this third reaction scheme starts with a nucleosid-3-yl-methylphosphondiisopropylamidite, XXXIVa, which is sulfhydrolyzed with $H_2S$ and tetrazole to yield XXIVa. Of course, other amino groups as previously defined by X may replace the diisopropyl group. Compound XXIVa may then be treated with XXXIIa in the presence of one equivalent iodine in pyridine to yield XXVIIIa, and the product purified by column chromatography. The choice of reaction solvent for the reaction with iodine is critical as essentially no product corresponding to XXVIIIa forms when the reaction is carried out in dichloromethane.

The preferred novel compounds of this aspect of the invention are those compounds of general formula XXI, XXIII, XXIV, and XXVII. These novel compounds may be used to prepare XXIX, the dinucleoside H-phosphonothioates. Compound XXIX may then be converted to preferably dinucleoside phosphorodithioates (XXVI), dinucleoside phosphorothioamidates and dinucleoside phosphorothioates. Compound XXI may also be condensed with an appropriate nucleoside, XXXIII, with iodine to form XXVI, the dinucleoside phosphorodithioate which can be converted to XXVII via a conventional alkylating agent. Preferred compound XXIII can react with an appropriate nucleoside, XXXIII, and a condensing agent such as triisopropylsulfonyl chloride, to form XXVII.

EXAMPLE IX

Synthesis of nucleoside 3'-hydrogenphosphonodithioate of the formula:

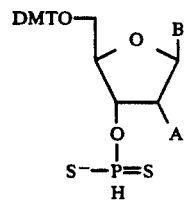

B = 1-Thyminyl;
B = 1-(N-4-benzoylcytosinyl);
B = 9-(N-6-benzoyladeninyl);
B = 9-(N-2-isobutyrylguaninyl); and
DMT = di-p-anisylphenylmethyl To a solution of 25 mmol of $PCl_3$ (2.18 ml, 3.43 g) in 250 ml $CH_2Cl_2$ containing 250 mmol (25.3 g, 27.5 ml) of N-methylmorpholine was added 83.35 mmol (5.75 g) of 1,2,4-triazole. The reaction mixture was stirred at room temperature for 30 minutes and cooled to 0° C. In this process the reaction mixture became turbid. $^{31}$P-NMR of the reaction mixture indicated complete formation of chloro-bis-triazolylphosphane (48.1 ppm). To this solution was added 5 mmol (2.73 g) of di-p-methoxytritylthymidine dissolved in 66 ml of dry $CH_2Cl_2$. After allowing the reaction mixture to come to room temperature in a period of 15 minutes, $H_2S$ gas was passed through it for an additional period of 15 minutes. During sulfhydrolysis, the reaction mixture became clear. After removal of excess $H_2S$ by passing argon gas through the product mixture, the solvents were evaporated in vacuo. The resulting yellow solid was taken up in $CH_2Cl_2$, and the solution extracted twice with 1M triethylammonium hydrogencarbonate. To remove the desired product ($^{31}$P-NMR: 87.5 ppm) from the hydrolysis products ($^{31}$P-NMR: 113.8 ppm, 52.7 ppm), the organic layer was subjected to chromatography ($CH_2Cl_2$/EtOZa/$CH_3OH$/$NEt_3$, 60:30:5:5, v:v:v:V) after being dried over $NaSO_4$. The product fractions were pooled and the product precipitated into n-pentane/ether, (9:1, V:V). The desired product was obtained in 56.6% yield (2.1 g).

EXAMPLE X

Synthesis of the dinucleoside phosphorodithioate of the formula:

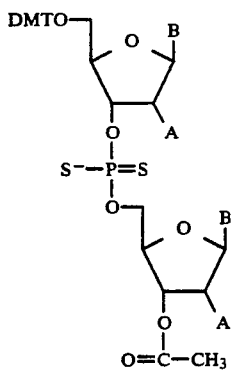

B = 1-Thyminyl;
B = 1-(N-4-benzoylcytosinyl);
B = 9-(N-6-benzoyladeninyl);
B = 9-(N-2-isobutyrylguaninyl); and
DMT = di-p-anisylphenylmethyl 0.1 mmol (74.19 mg) 5'-di-p-methoxytrityl-3'-hydrogenphosphonodithioate was dissolved in 0.9 ml of dry pyridine containing 0.12 mmol (28 mg) of 3'-acetylthymidine. To this solution was added dropwise 110 μl of a 1M solution of I$_2$ in pyridine. The reaction mixture decolorized instantly when the iodine was added. As the coupling was complete, a brown color persisted for at least 5 minutes. The $^{31}$P-NMR spectrum of the reaction mixture indicated two peaks: one of the desired product at 115.65 ppm, and a side product at 116.7 ppm (10%). After extraction with aqueous sodium bisulfite, which led to the disappearance of the peak caused by the side product, the mixture was subjected to column chromatography using CH$_3$CCl$_3$/CH$_3$OH/NEt$_3$ (85:14.5:0.5, v:v:v). The product fractions were combined and evaporated to dryness. Precipitation from CHCl$_3$ into n-pentane gave a white solid in 57% (63 mg) yield.

EXAMPLE XI

Synthesis of nucleoside phosphorodithioamidate of the formula:

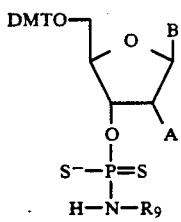

represented as XXVa wherein:
B = 1-Thyminyl;
B = 1-(N-4-benzoylcytosinyl);
B = 9-(N-6-benzoyladeninyl);
B = 9-(N-2-isobutyrylguaninyl);
R$_9$ = 2-anthracenyl; and
DMT = di-p-anisylphenylmethyl 0.1 mmol (74.19 mg) of 5'-di-p-methoxytritylthymidine 3'-hydrogenphosphonodithioate was dissolved in 0.9 ml of dry pyridine containing 0.12 mmol (23 mg) of 2-aminoanthracene. To this solution was added dropwise 110 μl of a 1M solution of I$_2$ in pyridine. The reaction mixture decolorized instantly when the iodine was added. As the coupling was complete, a brown color persisted for at least 5 minutes. The $^{31}$P-NMR spectrum of the reaction mixture indicated two peaks: one of the desired product at 95.5 ppm, and a side product at 105.4 ppm (10%). After extraction with aqueous sodium bisulfite, the mixture was subjected to column chromatography using CH$_3$CCl$_3$/CH$_3$OH/NEt$_3$ (85:14.5:0.5, v:v:v). The fluorescent product fractions were combined and evaporated to dryness. Precipitation from CHCl$_3$ into n-pentane gave a yellow solid in 47% (44 mg) yield.

EXAMPLE XII

Synthesis of nucleoside phosphorodithioate triester of the formula:

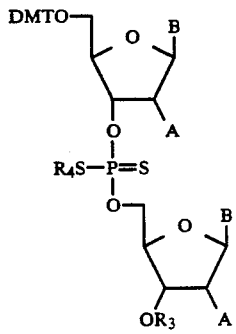

represented as XXVIIa wherein:
B = 1-Thyminyl;
B = 1-(N-4-benzoylcytosinyl);
B = 9-(N-6-benzoyladeninyl);
B = 9-(N-2-isobutyrylguaninyl);
R$_4$ = 2,4-dichlorobenzyl;
R$_3$ = acetyl; and
DMT = di-p-anisylphenylmethyl In order to introduce the phosphorodithioate linkage into oligonucleotides, a protection/deprotection scheme for the phosphorodithioate internucleotide linkage was developed. Thus, the dinucleoside phosphorodithioate XXVIa of Example X (57 mg, 0.06 mmol) was alkylated with alpha,2,4-trichlorotoluene (50 μl, 1 hr., 55° C.) in acetonitrile to yield the dinucleoside phosphorodithioate triester quantitatively. Further testing revealed that this was stable to reagents used in DNA synthesis (1% trifluoroacetic acid in dichloromethane and iodine in aqueous lutidine/THF), and that the phosphorodithioate triester was specifically S-dealkylated by treatment with thiophenolate (thiophenol:triethylamine:dioxane, 1:1:2, v:v:v, t$_\frac{1}{2}$=3 minutes at room temperature).

Conversion to a synthon useful for DNA synthesis was a two-step process. The dinucleoside phosphorodithioate triester was first deacylated (removal of the 3'-acetyl group) using 0.15M t-butylamine in methanol at 0° C. for 10 hours, and purified by silica gel chromatography. Less than 5% cleavage of the internucleotide linkage was observed. The deacylated compound was then reacted with bis(diisopropylamino)-2-cyanoethoxy phosphine (1,5 eq) in the presence of tetrazole (1 eq) for 1 hour at room temperature to produce the dinucleotide phosphorodithioate triester as the 3'-phosphoramidite in 76% yield. The resulting dinucleotide phosphoramidite has been used successfully in combination with modified mononucleoside phosphoramidites for the synthesis of a 26-mer DNA fragment containing the phosphorodithioate linkages between positions 8-9 (98.2% coupling efficiency). The synthesis was completed on silica based polymeric supports and phosphoramidite using the teachings contained in U.S. Pat. No. 4,415,732. The resulting oligonucleotide had the following sequence where the one phosphorodithioate linkage is marked by x instead of p: d(TpGpTpGpGpApApTxTpGpTpGpApGpCpGpGpApTpApApCpApApTpT)

EXAMPLE XIII

Synthesis of nucleoside hydrogenphosphonothioate of the formula:

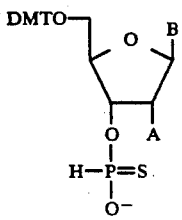

represented as XXIIa wherein:
B = 1-Thyminyl;
B = 1-(N-4-benzoylcytosinyl);
B = 9-(N-6-benzoyladeninyl);
B = 9-(N-2-isobutyrylguaninyl); and
DMT = di-p-anisylphenylmethyl 0.1 mmol of the compound according to formula XXIa (74.2 mg) was treated for 30 minutes with either 0.1 mmol of DCC and 1 mmol (18 μl) of water in 1 ml of pyridine, or 0.5 mmol of 2-chloro-1-methyl pyridinium iodide in pyridine. In both cases, the partial hydrolysis was complete. After evaporation of the reaction mixture to dryness, extraction with aqueous 1M triethylammonium hydrogencarbonate, the reaction mixture was subjected to column chromatography using $CH_3CCl_3/CH_3OH$ (4:1. v:v) containing 0.5% of triethylamine to yield the desired product.

EXAMPLE XIV

Synthesis of dinucleoside hydrogenphosphonothioate of the formula:

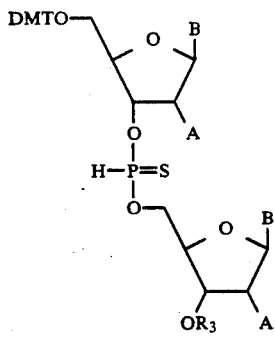

represented as XXIXa wherein:
B = 1-Thyminyl;
B = 1-(N-4-benzoylcytosinyl);
B = 9-(N-6-benzoyladeninyl);
B = 9-(N-2-isobutyrylguaninyl);
$R_3$ = acetyl; and
DMT = di-p-anisylphenylmethyl 0.1 mmol (74 mg) of 5'-dimethoxytritylthymidine 3'-hydrogenphospnonodithioate was dissolved in 1 ml of dry pyridine containing 0.1 mmol (28 mg) of 3'-acetylthymidine and 0.15 mmol (38 mg) of N-methyl-2-chloropyridiniumiodide. After 15 minutes, the $^{31}P$-NMR spectrum indicated the formation of mainly the desired product ($^{31}P$-NMR: 71.7 and 70.0 ppm), but also 5'-di-p-methoxytritylthymidine-3'-hydrogenphosphonothioate ($^{31}P$-NMR: 52.7 and 52.2 ppm) and unreacted starting material (16%). After evaporation to dryness and extraction with aqueous sodium bicarbonate and brine, the reaction mixture was subjected to column chromatography using $CH_3CCl_3/CH_3OH/NEt_3$ (90:9.5:.05, v:v:v). The product fractions were combined and evaporated to dryness. Precipitation from $CHCl_3$ into n-pentane produced a white solid product in 45% (40 mg) yield.

EXAMPLE XV

Synthesis of nucleoside S-(4-chlorobenzyl)phosphorodithioate of the formula:

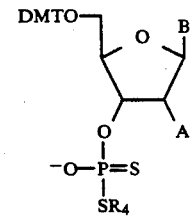

represented as XXIIIa wherein:
B = 1-Thyminyl;
B = 1-(N-4-benzoylcytosinyl);
B = 9-(N-6-benzoyladeninyl);
B = 9-(N-2-isobutyrylguaninyl);
$R_4$ = 4-chlorobenzyl; and
DMT = di-p-anisylphenylmethyl To a solution of 372.4 mg (0.5 mmol) of 5'-O-di-p-methoxytritylthymid-3'-yl-O-(β-cyanoethyl)phosphordiisopropylamidite in 2.5 ml dry and deoxygenated $CH_3CN$ was added 0.22 ml (0.262 g, 1.65 mmol) of 4-chlorobenzylmercaptan and a solution of 84,8 mg (1.2 mmol) of tetrazole in 2 ml of $CH_3CN$. The reaction mixture was stirred at room temperature under argon for 40 minutes, at which time a saturated solution of sulfur (2.25 ml) in toluene/2,6-lutidine (19/I) was added. The resulting mixture was allowed to continue to stir at room temperature for 1 hour. The mixture was then diluted with EtOAc and the organic layer was washed with 5% aqueous $NaHCO_3$, water and saturated NaCL, dried over $MgSO_4$, filtered, and evaporated. The crude residue obtained was dissolved in a minimum amount of $CH_2Cl_2$ and precipitated into pentane to give 0.4 g (96% yield) of colorless solid. Further purification by silica gel chromatography using $CH_3CCl_3/CH_3OH/NEt_3$ (97:2:1, v:v:v) resulted in a certain amount of β-cyanoethyl group cleavage, and thus pure product was not obtainable.

To a solution of 372.4 mg (0.5 mmol) of 5'-O-di-p-methoxytritylthymid-3'-yl-O-(β-cyanoethyl) S-4-chlorobenzenylphosphorodithioate in 2 ml of $NEt_3$ and 2 ml of $CH_3CN$ was stirred at room temperature for 5 hours. Solvent was removed by evaporation and the crude residue was purified by silica gel chromatography using $CH_2Cl_2/CH_3OH/NEt_3$ (95:3:1, v:v:v) to give 0.29 gram foamy compound XXIIIa as the triethylammonium salt (85.7% yield).

EXAMPLE XVI

Synthesis of dinucleoside phosphorodithioate of the formula:

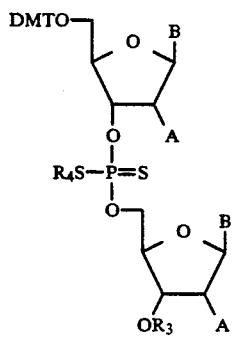

represented as XXVIIa wherein:
B=1-Thyminyl;
B=1-(N-4-benzoylcytosinyl);
B=9-(N-6-benzoyladeninyl);
B=9-(N-2-isobutyrylguaninyl);
$R_4$=4-chlorobenzyl;
$R_3$=acetyl; and
DMT=di-p-anisylphenylmethyl To a solution of 30 mg (34 μmol) of XXIII and 11.62 mg (1.2 eq) of 3'-O-acetylthymidine in 0.6 ml dry pyridine was added 30.9 mg (3 eq) of triisopropylbenzenesulfonyl chloride and 21 μl (21.6 mg; 7.7 eq) of 1-methylimidazole at room temperature under argon. The progress of the coupling reaction was monitored by $^{31}$P-NMR. After 25 minutes, the complete disappearance of the starting XXIIIa (71.7 and 71.2 ppm) and the formation of the pyrophosphorodithioate intermediate (81.4 and 81.1 ppm) and the desired XXVIIa (95.3 and 94.7 ppm) were observed. The reaction was complete after 2 hours at room temperature and its $^{31}$P-NMR only allowed 5 peaks at 99.1 ppm (8,3% intermediate, unidentified product), 95.0 and 94.4 ppm (89.2% intermediate, desired dimer 5'-O-di-p-methoxytritylthymidine-3'-O-(s-4-chlorobenzyl)-3'-O-(5'-O-thymidylyl-3'-O-acetyl)phosphorodithioate (XXVII), and 26.9 and 26.7 ppm (2.5% intermediate, undesired phosphorothioate dimer). The selectivity of the oxygen vs sulfur activation of XXIIIa in the above coupling reaction is 97.3:2.7.

EXAMPLE XVII

Synthesis of nucleoside methylthiophosphinate of the formula:

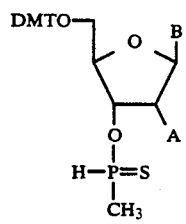

represented as XXIVa wherein:
B=1-Thyminyl;
B=1-(N-4-benzoylcytosinyl);
B=9-(N-6-benzoyladeninyl);
B=9-(N-2-isobutyrylguaninyl); and
DMT=di-p-anisylphenylmethyl 0.5 mmol (389 mg) of 5'-dimethoxytrityl-N-4-benxoyldeoxycytidine-3'-methylphosphonodiisopropylamidite was dissolved in 3 ml of dry acetonitrile. To this solution was added a solution of 2 mmol (140 mg) of tetrazole in acetonitrile. Subsequently, H$_2$S was passed through this solution for 5 minutes. The crude reaction mixture displayed two $^{31}$P-NMR signals at 70.7 and 70.5 ppm. The product mixture was then diluted with 50 ml of ethylacetate and was extracted with aqueous sodium bicarbonate and brine. After drying over sodium sulfate and removal of salt and solvents, the product was taken up in toluene and precipitated into n-pentane. The product was obtained in 94.1% yield (335 mg).

EXAMPLE XVIII

Synthesis of the dinucleoside methylphosphonothioate of the formula:

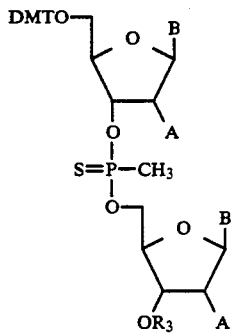

represented as XXIVa wherein:
B=1-Thyminyl;
B=1-(N-4-benzoylcytosinyl);
B=9-(N-6-benzoyladeninyl);
B=9-(N-2-isobutyrylguaninyl);
$R_3$=acetyl; and
DMT=di-p-anisylphenylmethyl 0.1 mmol (71.2 mg) 5'-dimethoxytrityl-N-4-benzoyldeoxycytidine-3'-hydrogenmethylthiophosphinate was dissolved in 9.0 ml of dry pyridine containing 0.1 mmol (28 mg) of 3'-acetylthymidine. To this solution was added, dropwise, 110 μl of a 1M solution of I$_2$ in pyridine. The reaction mixture decolorized within 2 minutes. As the coupling was complete, the brown color persisted for at least 5 minutes. The $^{31}$P-NMR spectrum of the reaction mixture indicated two peaks, one of the desired product at 98.06 and 97.18 ppm, and several side-products at 87.05 and 86.58 ppm (30%). After extraction with aqueous sodium bisulfite, the reaction mixture was subjected to column chromatography using CH$_3$CCl$_3$/CH$_3$OH (9:1, v:v). The product fractions were combined and evaporated to dryness. Precipitation from CHCl$_3$ into n-pentane followed. The product was obtained as a white solid in 47% (47 mg) yield. If the reaction was carried out in CH$_2$Cl$_2$, almost no formation of dimer was observed by $^{31}$P-NMR. Instead, several products giving NMR-signals from 85.3–93.4 ppm were formed.

Thus while we have illustrated and described the preferred embodiment of our invention, it is to be understood that this invention is capable of variation and modification and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview of the following claims.

Having thus described our invention and the manner and process of making and using it in such full, clear, concise, and exact terms so as to enable any person skilled in the art to which it pertains, or with it is most nearly connected, to make and use the same.

We claim:

1. A compound according to the formula:

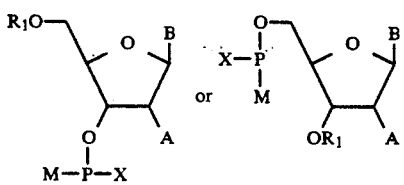

wherein B is a nucleoside or deoxynucleoside base;
wherein A is OH, H, halogen, SH, $NH_2$, azide, $OR_2$, $SR_2$ or $NR_2$ wherein $R_2$ is a heteroatom substituted or unsubstituted blocking group;
wherein $R_1$ is a blocking group;
wherein X is a secondary amino group of the formula $NR_6R_7$ wherein $R_6$ and $R_7$ taken separately each represent a heteroatom substituted or unsubstituted alkyl, aryl, aralkyl, cycloalkyl, cycloalkylalkyl, alkenyl, cycloalkenyl, aralkenyl, alkynyl, aralkynyl or cycloalkynyl, $R_6$ and $R_7$ when taken together form an alkylene chain containing up to 5 carbon atoms in the principle chain and a total of up to 10 carbon atoms with both terminal valence bonds of the chain being attached to the nitrogen atom, and when $R_6$ and $R_7$ are taken together with the nitrogen atom to which they are attached to form a nitrogen heterocycle including at least one additional heteroatom from the group nitrogen, oxygen, and sulfur; and
wherein M is sulfur single bonded to phosphorus and to $R_5$ wherein $R_5$ is a heteroatom substituted or unsubstituted alkyl, aryl, aralkyl, cycloalkyl, cycloalkylalkyl, alkenyl, cycloalkenyl, aralkenyl, alkynyl, aralkynyl or cycloalkynyl.

2. A compound according to the formula:

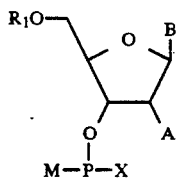

wherein B is a nucleoside or deoxynucleoside base;
wherein A is OH, H, halogen, SH, $NH_2$, azide, $OR_2$, $SR_2$, or $NR_2$ wherein $R_2$ is a heteroatom substituted or unsubstituted blocking group;
wherein $R_1$ is a blocking group;
wherein X is a secondary amino group of the formula $NR_6R_7$, wherein $R_6$ and $R_7$ taken separately each represent a heteroatom substituted or unsubstituted alkyl, aryl, aralkyl, cycloalkyl, cycloalkylalkyl, alkenyl, cycloalkenyl, aralkenyl, alkynyl, aralkynyl or cycloalkynyl, $R_6$ and $R_7$ when taken together form an alkylene chain containing up to 5 carbon atoms in the principal chain and a total of up to 10 carbon atoms with both terminal valence bonds of the chain being attached to the nitrogen atom to which $R_6$ and $R_7$ are attached, and when $R_6$ and $R_7$ are taken together with the nitrogen atom to which they are attached form a nitrogen heterocycle including at least one additional heteroatom from the group of nitrogen, oxygen, and sulfur; and
wherein M is sulfur single bonded to phosphorus and to $R_5$ where $R_5$ is a heteroatom substituted or unsubstituted alkyl, aryl, aralkyl, cycloalkyl, cycloalkylalkyl, alkenyl, cycloalkenyl, aralkenyl, alkynyl, aralkynyl or cycloalkynyl.

3. A compound according to claim 1 or 2 wherein $R_1$ is a trityl group.

4. A compound according to claim 1 or 2 wherein $R_1$ is a di-p-anisylphenylmethyl group.

5. A compound according to claim 1 or 2 wherein $R_1$ is a p-anisyldiphenylmethyl group.

6. A compound according to claim 1 or 2 wherein M is sulfur single-bonded to phosphorus and to $R_5$ where $R_5$ is benzyl.

7. A compound according to claim 1 or 2 wherein M is sulfur single-bonded to phosphorus and to $R_5$ is a substituted benzyl.

8. A compound according to claim 7 where M is sulfur single-bonded to phosphorus and to $R_5$ where $R_5$ is p-chlorobenzyl.

9. A compound according to claim 1 or 2 wherein M is sulfur single-bonded to phosphorus and to $R_5$ where $R_5$ is o,p-dichlorobenzyl.

10. A compound according to claim 9 wherein M is sulfur single-bonded to phosphorus and to $R_5$ where $R_5$ is heteroatom substituted lower alkyl.

11. A compound according to claim 10 wherein M is sulfur single-bonded to phosphorus and to $R_5$ where $R_5$ is β-cyanoethyl.

12. A compound according to claim 1 or 2 wherein X is a secondary amino group, $NR_6R_7$, where $R_6$ and $R_7$ are lower alkyl.

13. A compound according to claim 12 where X is diisopropylamino, dimethylamino, diethylamino and dibutylamino.

14. A compound according to claim 1 or 2 wherein B is adenine, guanine, cytosine uracil, and thymine.

15. The compound according to claim 2 wherein $R_1$ is di-p-anisylphenylmethyl, B is thyminyl, M is p-chlorobenzylmercaptyl, A is H, and X is diisopropylamino.

16. The compound according to claim 2 wherein $R_1$ is di-p-anisylphenylmethyl, B is 9-(N-6-benzoyladeninyl), M is p-chlorobenzylmercaptyl, A is H, and X is diisopropylamino.

17. The compound according to claim 2 wherein $R_1$ is di-p-anisylphenylmethyl, B is 1-(N-4-benzoylcytosinyl), M is p-chlorobenzylmercaptyl, A is H, and X is diisopropylamino.

18. The compound according to claim 2 wherein $R_1$ is di-p-anisylphenylmethyl, B is 9-(N-2-isobutyrylguaninyl), M is p-chlorobenzylmercaptyl, A is H, and X is diisopropylamino.

19. A compound according to claim 1 wherein X is selected from the group consisting of dimethylamino, diethylamino, diisopropylamino, dibutylamino, methylpropylamino, methylhexylamino, methylcyclohexylamino, ethylcyclopropylamino, methylbenzylamino, methylphenylamino, ethylchloroethylamino, methyltoluyamino, methyl-p-chlorophenylamino, methylcyclohexylmethylamino, bromobutylcyclohexylamino, methyl-p-cyanophenylamino, ethyl-β-cyanoethylamino, morpholino, thiomorpholino, pyrrolidino, piperidino, 2,6-dimethylpiperidino and piperazino.

20. A compound according to claim 1 wherein X is diisopropylamino.

21. A compound according to claim 2 wherein X is selected from the group consisting of dimethylamino, diethylamino, diisopropylamino, dibutylamino, methylpropylamino, methylhexylamino, methycyclohexylamino, ethylcyclopropylamino, methylbenzylamino, methylphenylamino, ethychloroethylamino, methyltoluylamino, methyl-p-chlorophenylamino, methylcyclohexylmethylamino, bromobutylcyclohexylamino, methyl-p-cyanophenylamino, ethyl-cyanoethylamino, morpholino, thiomorpholino, pyrrolidino, piperidino, 2,6-dimethylpiperidino and piperazino.

22. A compound according to claim 2 wherein X is diisopropylamino.

23. A compound according to claim 1 where M is selected from a group consisting of ethylmercaptyl, methylmercaptyl, propylmercaptyl, butylmercaptyl, β-cyanoethylmercaptyl, benzylmercaptyl, p-chlorophenylmercaptyl, p-chlorobenzylmercaptyl, 2,4-dichlorobenzylmercaptyl, cyclohexylmercaptyl, and p-nitrophenylethylmercaptyl.

24. A compound according to claim 1 where M is p-chlorobenzylmercaptyl.

25. A compound according to claim 2 where M is selected from a group consisting of ethylmercaptyl, methylmercaptyl, propylmercaptyl, butylmercaptyl, β-cyanoethylmercaptyl, benzylmercaptyl, p-chlorophenylmercaptyl, p-chlorobenzylmercaptyl, 2,4-dichlorobenzylmercaptyl, cyclohexylmercaptyl, and p-nitrophenylethylmercaptyl.

26. A compound according to claim 2 where M is p-chlorobenzylmercaptyl.

* * * * *

UNITED STATES PATENT AND TRADEMARK OFFICE
CERTIFICATE OF CORRECTION

PATENT NO. : 5,218,103
DATED : June 8, 1993
INVENTOR(S) : Marvin H. Caruthers, Yun-Xi Ma, Eric K. Yau, John Nielsen and Wolfgang Brill It is certified that error appears in the above-identified patent and that said Letters Patent is hereby corrected as shown below:

Column 1, line 25, "nucleosid-", should be -- nucleoside- --.

Column 3, line 68, "and" should be -- or --.

Column 4, line 13, "phosphorus" should be -- phosphorus double --.

Column 4, line 15, "phosphorus" should be -- phosphorus double bonded to sulfur and single bonded to T, G, X or M. The substitutent T is oxygen single bonded to phosphorus --.

Column 5, line 3, "quanine" should be -- guanine --.

Column 5, line 50 "ad" should be -- and --.

Column 6, lines 1 to 3, "carbon at ... respectively." should be deleted.

Column 6, lines 10 to 12, "The cyclic ... the cycle." should be deleted.

Column 6, line 25, "can be replaced " should be -- can replace --.

Column 6, line 58, "heteroatoms" should be -- heteroatom --.

Column 6, line 66, "PS2" should be -- P(SH)S --.

Column 7, lines 1-15 should be:

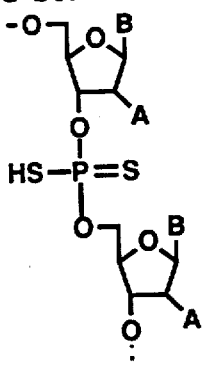

UNITED STATES PATENT AND TRADEMARK OFFICE
CERTIFICATE OF CORRECTION

PATENT NO. : 5,218,103  Page 2 of 4
DATED : June 8th 1993
INVENTOR(S) : Caruthers et al It is certified that error appears in the above-identified patent and that said Letters Patent is hereby corrected as shown below:

Column 7, line 20, "OPOS" should be -- OP(OH)S --.

Column 7, lines 25 to 38 should be

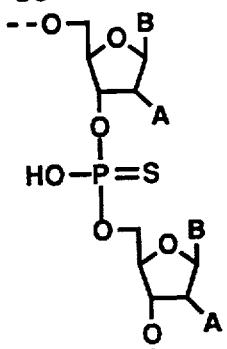

Column 8, line 18, "or" should be -- or O- --.

Column 8, line 20, "3"" should be -- 3' --.

Column 15, line 62, "M" should be -- T --.

Column 16, line 10, "M" should be -- T --.

Column 16, line 20, "G" should be -- Z --.

Column 16, line 21, "B" should be -- M --.

Column 17, line 28, "phosphorodithiosate" should be -- phosphorodithioate --.

Column 17, line 39, "dieter" should be -- diester --.

Column 17, line 47, "-bis(dialkylaminophosphine," should be -- -bis(dialkylamino)phosphine, --.

Column 18, line 68, "sited" should be -- sites --.

UNITED STATES PATENT AND TRADEMARK OFFICE
CERTIFICATE OF CORRECTION

PATENT NO. : 5,218,103
DATED : June 8th 1993
INVENTOR(S) : Caruthers et al

It is certified that error appears in the above-identified patent and that said Letters Patent is hereby corrected as shown below:

Column 20, line 6, "PCl13" should be -- PCl3 --.

Column 21, line 3, "phosphorothioamidate" should be -- phosophorothioamidite --.

Column 21, line 43, "5'-1-di" should be -- 5'-O-di --.

Column 22, line 38, "triethylamino" should be -- triethylamine --.

Column 22, ilne 44, processed" should be -- proceeded --.

Column 23, lines 5 to 21 should be:

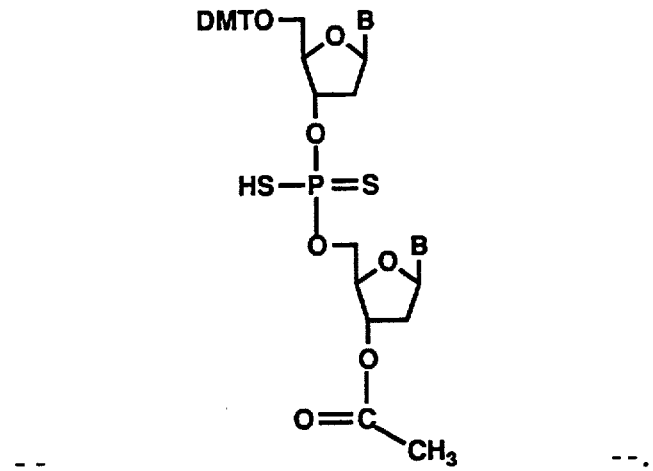

Column 24, line 55, "of" should be -- to a --.

Column 25, line 25, "pApTpApApCpApAptpt)" should be -- pApTpApApCpApApTpT) --.

Column 27, line 37, "timed" should be -- times --.

Column 28, lines 40 and 41, "and ... phosphorodiamidite" should be deleted.

UNITED STATES PATENT AND TRADEMARK OFFICE
CERTIFICATE OF CORRECTION

PATENT NO. : 5,218,103

DATED : June 8th 1993

INVENTOR(S) : Caruthers et al

It is certified that error appears in the above-identified patent and that said Letters Patent is hereby corrected as shown below:

Column 28, line 68, "represented" should be -- represented more --.

Column 29, line 2, "Ia" should be -- Ib --.

Column 37, line 51, "XXXIVa" should be -- XXXIa --.

Column 37, line 55, "XXXIIa" should be -- XXXIIIa --..

Column 41, line 68, "hydrogenphospnonodithioate" should be -- hydrogen phosphonodithioate --.

Column 44, line 2, "benx" should be -- benz --.

Signed and Sealed this

Sixth Day of September, 1994

Attest:

BRUCE LEHMAN

Attesting Officer     Commissioner of Patents and Trademarks